US009646261B2

(12) United States Patent
Agrafioti et al.

(10) Patent No.: US 9,646,261 B2
(45) Date of Patent: May 9, 2017

(54) ENABLING CONTINUOUS OR INSTANTANEOUS IDENTITY RECOGNITION OF A LARGE GROUP OF PEOPLE BASED ON PHYSIOLOGICAL BIOMETRIC SIGNALS OBTAINED FROM MEMBERS OF A SMALL GROUP OF PEOPLE

(75) Inventors: Foteini Agrafioti, Toronto (CA); Francis Minhthang Bui, Saskatoon (CA); Dimitrios Hatzinakos, Toronto (CA)

(73) Assignee: Nymi Inc., Toronto (CA)

( * ) Notice: Subject to any disclaimer, the term of this patent is extended or adjusted under 35 U.S.C. 154(b) by 449 days.

(21) Appl. No.: 14/116,058

(22) PCT Filed: May 10, 2012

(86) PCT No.: PCT/CA2012/000448
§ 371 (c)(1),
(2), (4) Date: Feb. 7, 2014

(87) PCT Pub. No.: WO2012/151680
PCT Pub. Date: Nov. 15, 2012

(65) Prior Publication Data
US 2014/0188770 A1 Jul. 3, 2014

Related U.S. Application Data

(60) Provisional application No. 61/484,470, filed on May 10, 2011.

(51) Int. Cl.
*G06F 15/18* (2006.01)
*G06N 99/00* (2010.01)
(Continued)

(52) U.S. Cl.
CPC ............ *G06N 99/005* (2013.01); *A61B 5/117* (2013.01); *A61B 5/7267* (2013.01);
(Continued)

(58) Field of Classification Search
CPC ........................................... G06K 2009/00939
(Continued)

(56) References Cited

U.S. PATENT DOCUMENTS 5,490,139 A  2/1996  Baker et al.
6,041,410 A  3/2000  Hsu et al.
(Continued)

FOREIGN PATENT DOCUMENTS

WO  2004012388 A1  2/2004
WO  2005117527 A3  4/2006
(Continued)

OTHER PUBLICATIONS

Pasini et al., "Sas-based Authenticated Key Agreement," in Public Key Cryptography—PKC 2006, pp. 395-409, Springer, 2006.
(Continued)

*Primary Examiner* — David Vincent
(74) *Attorney, Agent, or Firm* — John W. Branch; Lowe Graham Jones PLLC

(57) ABSTRACT

The present invention is a biometric security system and method operable to authenticate one or more individuals using physiological signals. The method and system may comprise one of the following modes: instantaneous identity recognition (MR); or continuous identity recognition (CIR). The present invention may include a methodology and framework for biometric recognition using physiological signals and may utilize a machine learning utility. The machine learning utility may be presented and adapted to the needs of different application environments which constitute different application frameworks. The present invention may
(Continued)

further incorporate a method and system for continuous authentication using physiological signals and a means of estimating relevant parameters.

22 Claims, 12 Drawing Sheets

(51) Int. Cl.

| | |
|---|---|
| A61B 5/117 | (2016.01) |
| G06F 21/31 | (2013.01) |
| G06F 21/32 | (2013.01) |
| G06K 9/00 | (2006.01) |
| A61B 5/00 | (2006.01) |
| A61B 5/04 | (2006.01) |
| H04L 29/06 | (2006.01) |

(52) U.S. Cl.
CPC .......... *G06F 21/316* (2013.01); *G06F 21/32* (2013.01); *G06K 9/00006* (2013.01); *G06K 9/00885* (2013.01); *A61B 5/04012* (2013.01); *G06K 2009/00939* (2013.01); *H04L 63/0861* (2013.01)

(58) Field of Classification Search
USPC ...................................... 706/12, 45
See application file for complete search history.

(56) References Cited

U.S. PATENT DOCUMENTS

| | | | |
|---|---|---|---|
| 6,418,424 B1* | 7/2002 | Hoffberg | G06F 3/00 386/E5.004 |
| 6,580,356 B1 | 6/2003 | Alt et al. | |
| 6,799,726 B2 | 10/2004 | Stockhammer | |
| 7,023,320 B2 | 4/2006 | Dvorak | |
| 7,095,707 B2 | 8/2006 | Rakib et al. | |
| 7,378,939 B2 | 5/2008 | Sengupta et al. | |
| 7,689,833 B2 | 3/2010 | Lange | |
| 7,780,080 B2 | 8/2010 | Owen et al. | |
| 7,814,332 B2 | 10/2010 | Beenau et al. | |
| 8,352,730 B2 | 1/2013 | Giobbi | |
| 8,371,501 B1 | 2/2013 | Hopkins | |
| 8,412,949 B2 | 4/2013 | Giobbi et al. | |
| 8,468,362 B2 | 6/2013 | Konetski et al. | |
| 8,869,263 B2 | 10/2014 | Pasquero et al. | |
| 8,994,498 B2 | 3/2015 | Agrafioti et al. | |
| 9,189,901 B2 | 11/2015 | Agrafioti et al. | |
| 9,349,235 B2 | 5/2016 | Agrafioti et al. | |
| 2002/0140542 A1 | 10/2002 | Prokoski et al. | |
| 2003/0046228 A1 | 3/2003 | Berney | |
| 2003/0135097 A1* | 7/2003 | Wiederhold | A61B 5/02055 600/301 |
| 2005/0068171 A1 | 3/2005 | Kelliher et al. | |
| 2006/0090909 A1* | 5/2006 | Carter | G07F 19/20 172/111 |
| 2007/0016088 A1 | 1/2007 | Grant et al. | |
| 2007/0049267 A1 | 3/2007 | Kota et al. | |
| 2007/0063548 A1* | 3/2007 | Eipper | G06K 9/6284 296/203.01 |
| 2007/0177770 A1 | 8/2007 | Derchak et al. | |
| 2007/0186105 A1 | 8/2007 | Bailey et al. | |
| 2008/0091681 A1* | 4/2008 | Dwivedi | G06F 21/554 |
| 2008/0216171 A1 | 9/2008 | Sano et al. | |
| 2008/0253626 A1* | 10/2008 | Shuckers | G06K 9/00114 382/125 |
| 2008/0294907 A1 | 11/2008 | Hively | |
| 2009/0037983 A1* | 2/2009 | Chiruvolu | G06F 21/31 726/4 |
| 2009/0146947 A1 | 6/2009 | Ng | |
| 2009/0199264 A1 | 8/2009 | Lang | |
| 2010/0030695 A1 | 2/2010 | Chen et al. | |
| 2010/0306106 A1 | 12/2010 | Dagan | |
| 2010/0311482 A1* | 12/2010 | Lange | A61B 5/0404 463/1 |
| 2010/0325218 A1* | 12/2010 | Castro | G06Q 50/01 709/206 |
| 2012/0004523 A1 | 1/2012 | Richter et al. | |
| 2012/0060030 A1* | 3/2012 | Lamb | H04L 63/0876 713/166 |
| 2012/0123232 A1* | 5/2012 | Najarian | A61B 5/0022 600/345 |
| 2012/0198277 A1* | 8/2012 | Busser | H04L 63/1416 714/26 |
| 2012/0316406 A1 | 12/2012 | Rahman et al. | |
| 2012/0317024 A1 | 12/2012 | Rahman et al. | |
| 2013/0159021 A1 | 6/2013 | Felsher | |
| 2013/0322622 A1 | 12/2013 | Bailey et al. | |
| 2014/0188770 A1 | 7/2014 | Agrafioti et al. | |
| 2015/0028996 A1 | 1/2015 | Agrafioti et al. | |

FOREIGN PATENT DOCUMENTS

| | | |
|---|---|---|
| WO | 2007128975 A2 | 11/2007 |
| WO | 2012151680 | 11/2012 |

OTHER PUBLICATIONS

Noble et al.. "The Case for Transient Authentication," Department of Electrical Engineering and Computer Science, University of Michigan, Ann Arbor, MI, 6 pages.

Ojala et al., "Wearable Authentication Device for Transparent Login in Nomadic Applications Environment," 2008 International Conference on Signals, Circuits and Systems, 6 pages.

Al-Muhtadi et al., "Wearable Security Services," Department of Computer Science, 6 pages.

Bellare et al., "Forward-Security in Private-Key Cryptography," Department of Computer Science and Engineering, 2003, pp. 1-24.

Agrafioti et al., "Medical Biometrics in Mobile Health Monitoring," Security and Communication Networks, 2011, 4, pp. 525-539.

Hoekema et al., "Geometrical Aspects of the Interindividual Variability of Multilead ECG Recordings," IEEE Transactions on Biometrical Engineering, vol. 48, No. 5, May 2001, pp. 551-559.

Draper et al., "The Corrected Orthogonal Electrocardiogram and Vectorcardiogram in 510 Normal Men (Frank Lead System)" Circulation, vol. 30, 1964, pp. 853-864.

Biel et al., "ECG Analysis: A New Approach in Human Identification," IEEE Transactions on Instrumentation and Measurement, vol. 50, No. 3, Jun. 2001, pp. 808-812.

Wubbeler et al., "Verification of Humans Using the Electrocardiogram," Pattern Recognition Letter, vol. 28, No. 10, 2007, pp. 1172-1175.

Odinaka et al., "ECG Biometrics: A Robust Short-time Frequency Analysis," Proceedings of IEEE International Workshop on Information Forensics and Security, Dec. 2010, pp. 1-6.

Li et al., "Robust ECG Biometrics by Fusing Temporal and Cepstral Information," Proceedings of 20th International Conference on Pattern Recognition, Aug. 2010, pp. 1326-1329.

Agrafioti et al., "ECG Based Recognition Using Second Order Statistics," Communication Networks and Services Research Conference, May 2008, pp. 82-87.

Agafioti et al., "Heart Biometrics: Theory, Methods, and Applications," Intech, www.intechopen.com, 19 pages.

Agrafioti et al., "Signal Validation for Cardiac Biometrics," IEEE 35th International Conference on Acoustics, Speech, and Signal Processing, 2010, pp. 1734-1737.

Zhao et al., "Fingerprint Image Synthesis Based on Statistical Feature Models," IEEE 5th International Conference on Biometrics: Theory, Applications, and Systems, 2012, pp. 23-30.

Agrafioti et al., "Medical Biometrics: The Perils of Ignoring Time Dependency," Proceedings of 3rd International Conference on Biometrics: Theory, Applications, and Systems, 2009, pp. 1-6.

Odinaka et al., "ECG Biometric Recognition: A Comparative Analysis" IEEE Transactions on Information Forensics and Security, vol. 7, No. 6, Dec. 2012, pp. 1812-1824.

(56) References Cited

OTHER PUBLICATIONS

Office Communication for U.S. Appl. No. 14/461,881 mailed on Oct. 27, 2014, 18 pages.
International Search Report and Written Opinion for International Application No. PCT/IB2014/001383 mailed on Dec. 8, 2014, 11 pages.
Official Communication for U.S. Appl. No. 14/949,509 mailed on Feb. 2, 2016 (17 pages).
Official Communication for U.S. Appl. No. 14/340,414 mailed on Jan. 22, 2015.
Official Communication for U.S. Appl. No. 14/461,881 mailed on Feb. 12, 2015.
Supplementary European Search report and Search Opinion for EP application 12782151.0 mailed on Mar. 12, 2015 (7 pages).
Office Communication for U.S. Appl. No. 14/670,316 mailed on May 8, 2015 (20 pages).
Canadian Intellectual Property Office, ISA/CA, International Search Report dated Aug. 23, 2012, issued in International Application No. PCT/CA2012/000448.
Wang et al., "Analysis of Human Electrocardiogram for Biometric Recognition", EURASIP Journal on Advances in Signal Processing, vol. 2008, Article ID 148658, pp. 1-11, Jan. 31, 2008.
Klosterman et al. "Secure Continuous Biometric-Enhanced Authentication", CMU-CS-00-134, School of Computer Science, Carnegie Mellon University, pp. 1-22, May 31, 2000.
Ortega-Garcia, et al., "MCYT Baseline Corpus: A Bimodal Biometric Database", IEE Proc.-Vis. Image Signal Process, vol. 150, No. 6, pp. 395-401. Dec. 31, 2003.
Official Communication for U.S. Appl. No. 14/675,489 mailed on Jun. 11, 2015 (24 pages).
Official Communication for U.S. Appl. No. 14/942,919 mailed on Mar. 30, 2016 (14 pages).
European Search Report for Application No. 16162764.1 mailed on Aug. 5, 2016, (9 pages).
Official Communication for U.S. Appl. No. 15/162,109 mailed on Aug. 10, 2016, (14 pages).
Official Communication for U.S. Appl. No. 14/949,509 mailed on Jun. 7, 2016, (11 pages).

* cited by examiner

ENABLING CONTINUOUS OR INSTANTANEOUS IDENTITY RECOGNITION OF A LARGE GROUP OF PEOPLE BASED ON PHYSIOLOGICAL BIOMETRIC SIGNALS OBTAINED FROM MEMBERS OF A SMALL GROUP OF PEOPLE

FIELD OF INVENTION

This invention relates in general to the field of biometric security and more particularly to biometric security using physiological signals to achieve instantaneous identity recognition and continuous identity recognition.

BACKGROUND OF THE INVENTION

Biometric recognition was introduced as a more secure means of identity establishment. Biometric modalities are characteristics of the human body that are unique for every individual and that can be used to establish the identity of a person in a population. These characteristics can be either physiological or behavioral. For instance, the face, the iris and the fingerprints are physiological biometric modalities. Keystroke dynamics, the gait and the voice are examples of behavioral biometric modalities. The fact that biometric modalities are directly linked with individual users presents an opportunity to bridge the security gaps caused by traditional recognition strategies. Biometric modalities are difficult to steal or counterfeit when compared to PIN numbers or passwords. In addition, the convenience of not having to carry a piece of ID or remember a password can make biometric systems more accessible and easy to use.

An important consideration with regards to biometric technologies is the robustness to circumvention and replay attacks. Circumvention is a form of biometric forgery, for example such as falsified fingerprints that are reproduced from an original fingerprint. A replay attack is the presentation to the system of the original biometric feature from an illegitimate subject, for example such as pre-recorded voice playbacks in speaker recognition systems. Biometric obfuscation is another prominent risk, whereby biometric features are intentionally removed or damaged to avoid establishment of the true identity. For example, fingerprints can be intentionally altered to avoid identification. With the wide deployment of biometrics, these attacks are becoming frequent and concerns are being raised regarding the security levels that known biometric security technologies are capable of offering.

Concentrated efforts have been made to develop a next generation of biometric security technologies based on biometric characteristics that are inherently robust and that counter the above mentioned attacks. For example, in this pursuit, characteristics that are internal to the human body have been investigated, such as vein patterns and cognitive biometrics. Physiological signals constitute another category of new biometric modalities. Physiological signals encompass signals which are typically used in clinical diagnostics. Some examples of medical biometric signals are the electrocardiogram (ECG), phonocardiogram (PPG), electroencephalogram (EEG), blood volume pressure (BVP) and electromyogram (EMG).

A number of United States patents discuss biometric identification using physiological signals. The most commonly explored modality is the electrocardiogram (ECG). For example, U.S. Pat. No. 7,689,833 and U.S. Patent Application Publication No. 2010/0311482 present a method for the creation of a "grand-average" ECG signal, whereby users are identified based on how different they appear from the average.

U.S. Patent Application Publication No. 2004/0249294 discusses a similar idea for pre-determining an average feature vector, but in the frequency domain.

U.S. Patent Application Publication No. 2010/0090798 isolates and aligns pulse segments on ECG and PPG signals for biometric template design.

U.S. Pat. No. 7,630,521 discusses an artificial neural network (ANN) for the design of ECG biometric templates.

U.S. Pat. No. 7,796,01 describes a methodology for user authentication on smart-cards.

U.S. Patent Application Publication No. 2010/0113950 discusses user identification using cardiac signals on electronic devices with embedded sensors.

Various approaches to feature extraction for biometric recognition from ECG signals have been published in academic journals. These approaches can be categorized as either fiducial points dependent or independent, based on the type of features that comprise the biometric template. For example, in S. A. Israel, J. M. Irvine, A. Cheng, M. D. Wiederhold, and B. K. Wiederhold, "ECG to identify individuals," Pattern Recognition, vol. 38, no. 1, pp. 133-142, 2005.", a fiducial dependent methodology was proposed where the biometric template comprised of temporal characteristics of heart beats.

An academic publication K. S. Kim, T. H. Yoon, J. L., D. J. Kim, and H. S. Koo, "A robust human identification by normalized time-domain features of Electrocardiogram," in Proceedings of 27th Annual Int. Conf on Eng. in Medicine and Biology Society, January 2005, pp. 1114-1117, proposed a method to normalize time domain features by Fourier synthesizing an up-sampled ECG heart beat.

A delineation method for particular ECG waveforms was proposed by Y. Singh and P. Gupta, "ECG to individual identification," in Proceedings of IEEE Int. Conf. on Biometrics: Theory, Applications and Systems, October 2008, pp. 1-8.

Fiducial independent approaches have also been proposed. For example, G. Wübbeler, M. Stavridis, D. Kreiseler, R. D. Bousseljot, and C. Elster, "Verification of humans using the electrocardiogram," Pattern Recogn. Lett., vol. 28, no. 10, pp. 1172-1175, 2007, combined different ECG leads into a two-dimensional heart vector which was used for biometric matching.

Can Ye, M. T. Coimbra, and B. V. K. V. Kumar, "Investigation of human identification using two-lead electrocardiogram (ECG) signals," in Fourth IEEE International Conference on Biometrics: Theory Applications and Systems, September 2010, pp. 1-8, applied the discrete wavelet transform for ECG biometric recognition.

Another fiducial independent approach was discussed by N. Ghofrani and R. Bostani, "Reliable features for an ECG-based biometric system," in *Proceedings of 17th Iranian Conference of Biomedical Engineering*, November 2010, pp. 1-5. This approach used an autoregressive model and the power spectral density of ECG segments for biometric matching.

Additional academic publications discussing relevant prior art include the following. F. Agrafioti, D. Hatzinakos, "ECG based recognition using second order statistics", *IEEE 6th Annual Conference on Communication Networks and Services Research*, pp. 82-87, May 2008. This publication presented a method to ECG biometric feature extraction using the Autocorrelation (AC) and the Linear Discriminant Analysis (LDA).

F. Agrafioti and D. Hatzinakos, "Fusion of ECG sources for human identification," in Third International Symposium on Communications, Control and Signal Processing (ISCCSP), Malta, March 2008, discusses a method to information fusion from various ECG leads which does not relate to the present invention.

F. Agrafioti, F. M. Bui, D. Hatzinakos, "On Supporting Anonymity in a BAN Biometric Framework", 16*th Int. Conf. on Digital Signal Processing*, pp. 1-6, 2009; and "F. Agrafioti, F. M. Bui, and D. Hatzinakos, "Medical biometrics: The perils of ignoring time dependency," in IEEE 3rd International Conference on Biometrics: Theory, Applications, and Systems, Washington, DC, USA, September 2009, pp. 1-6; and F. Agrafioti, F. M. Bui, D. Hatzinakos, "Medical Biometrics in Mobile Health Monitoring", *Security and Communication Networks, Special Issue on Biometric Security for Mobile Computing*, Wiley, vol. 4, no. 2, pp. 525-539, 2011. These publications discuss a biometric encryption solution for ECG biometric systems and a method for template updating.

F. Agrafioti, D. Hatzinakos, "Signal Validation for Cardiac Biometrics", *IEEE* 35*th Int. Conf. on Acoustics, Speech, and Signal Processing*, pp. 1734-1737, March 2010, that discusses signal processing.

F. Agrafioti and D. Hatzinakos, "ECG biometric analysis in cardiac irregularity conditions," Signal, Image and Video Processing, pp. 1863-1703, 2008, that discusses robustness of the autocorrelation method to common cardiac disorders.

F. Agrafioti, J. Gao, D. Hatzinakos, "Heart Biometrics: Theory, Methods and Applications", in *Biometrics: Book* 3, J. Yang, Eds., Intech, that is essentially a review of the relevant academic literature without new components in the method or framework for ECG biometric recognition.

Other relevant prior art journal articles include: F. Agrafioti, F. M. Bui, D. Hatzinakos, "Medical Information Management with ECG Biometrics: A Secure and Effective Framework", in *Handbook on Ambient Assisted Living for Healthcare, Well-being and Rehabilitation*, Paul McCullagh, IOS Press; G. Kozmann, R. L. Lux, and L. S. Green, "Geometrical factors affecting the interindividual variability of the ECG and the VCG," J. Electrocardiology, vol. 33, pp. 219-227, 2000; R. Hoekema, G. Uijen, and A. van Oosterom, "Geometrical aspect of the interindividual variaility of multilead ECG recordings," IEEE Trans. Biomed. Eng., vol. 48, pp. 551-559, 2001; and H. Draper, C. Peffer, F. Stallmann, D. Littmann, and H. Pipberger, "The corrected orthogonal electrocardiogram and vectorcardiogram in 510 normal men (frank lead system)," Circulation, vol. 30, pp. 853-864, 1964.

SUMMARY OF THE INVENTION

In one aspect, the present disclosure relates to a biometric security system operable to authenticate one or more individuals, said system characterized in that it comprises: a device operable to obtain one or more physiological signals of each of the one or more individuals; a machine learning utility connected to the device, said machine learning utility being operable to biometrically process the one or more physiological signals to determine the variability of each of the one or more physiological signals, and to identify or verify the identity of each of the one or more individuals; and one or more databases connected to the machine learning utility operable to store one or more biometrically processed physiological signals.

Said biometric security system characterized in that the machine learning utility may be operable in any of the following modes: continuous identity recognition mode; and instantaneous recognition mode.

Said biometric security system characterized in that the device may be operable to obtain the one or more physiological signals of the one or more individuals on a continuous basis during a period of time when operating in the continuous identity recognition mode.

Said biometric security system characterized in that the device may incorporate a display means operable to display the authentication results of the system to each of the one or more individuals.

Said biometric security system characterized in that the device may incorporate an input means operable for any of the one or more individuals to input an identity claim to provide identification data that is any of the following: a name; a password; a device ID number; and other non-biometric data identifying the one of the one or more individuals inputting the identity claim.

Said biometric security system characterized in that the one or more databases may include any of the following: a generic database, an enrollee database, or an enrollee and generic database.

Said biometric security system characterized in that the generic database may be operable to store one or more template biometric signals generated by a biometric template design module so that the one or more template biometric signals are accessible by the machine learning utility to determine the variability of each of the one or more physiological signals in a population.

Said biometric security system characterized in that it may be a distributed system or a centralized system.

Said biometric security system characterized in that a variability estimation means operable to generate a threshold output may be connected to the machine learning utility.

Said biometric security system characterized in that any of the following may be connected to the machine learning module and are operable to biometrically process the one or more physiological signals: a filter module; an AC module; and an outlier removal module.

Said biometric security system characterized in that a feature projection module may be incorporated in an identification or verification mode of the system to apply a transformation rule to biometrically process the one or more physiological signals, said feature projection module being connected to a matching module.

Said biometric security system characterized in that the feature projection module may be connected to any of: a one-to-many matching module operable to determine the identity of the one of the one or more individuals relating to the one or more physiological signals in the identification mode of the system; and a one-to-one matching module operable to receive an identity claim and to utilize the identity claim to determine whether one of the one or more physiological signals is that of one of the one or more individuals.

Said biometric security system characterized in that it may be operable in a large-scale framework or a small-scale framework.

In another aspect, the present disclosure relates to a biometric security method to authenticate one or more individuals, said method characterized in that it comprises the steps of: receiving one or more physiological signals; pre-processing each of the one or more physiological signals to generate a biometrically processed signal; extracting features from the biometrically processed signal to generate a set of signal features; and classifying the set of signal features to identify or verify the identity of each of the one or more individuals.

Said biometric security method characterized in that it may comprise the further steps of: pre-processing each of the one or more physiological signals to generate the biometrically processed signal by any of the steps of: filtering and windowing; extracting features of the biometrically processed signal to generate the set of signal features by any of the steps of: autcorrelation estimation; outlier removal; and machine learning incorporating linear discriminant analysis; and classifying the set of signal features by any of the steps of: matching; individual confidence estimation; and cumulative confidence estimation.

Said biometric security method characterized in that it may comprise the further step of continuously receiving the one or more physiological signal relating to at least one of the one or more individuals during a time period and repeating the following steps for each of the one or more physiological signals to perform continuous recognition identification of at least one of the one or more individuals: pre-processing each of the one or more physiological signals to generate a biometrically processed signal; extracting features from the biometrically processed signal to generate a set of signal features; and classifying the set of signal features to identify or verify the identity of each of the one or more individuals.

Said biometric security method characterized in that it may comprise the further step of receiving an identity claim from at least one of the one or more individuals and utilizing the identity claim in the verification of the identity of the one of the one or more individuals who provided the identity claim.

Said biometric security method characterized in that it may comprise the further step of generating any of: a transformation rule; and a threshold.

Said biometric security method characterized in that it may comprise the further step of applying a biometric algorithm or calculation to identify or verify the identity each of the one or more individuals.

Said biometric security method characterized in that it may comprise the further step of performing biometric confidence analysis in any of the following manners: continuously; and cumulatively.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

The invention will be better understood and objects of the invention will become apparent when consideration is given to the following detailed description thereof. Such description makes reference to the annexed drawings wherein.

Figure 1:
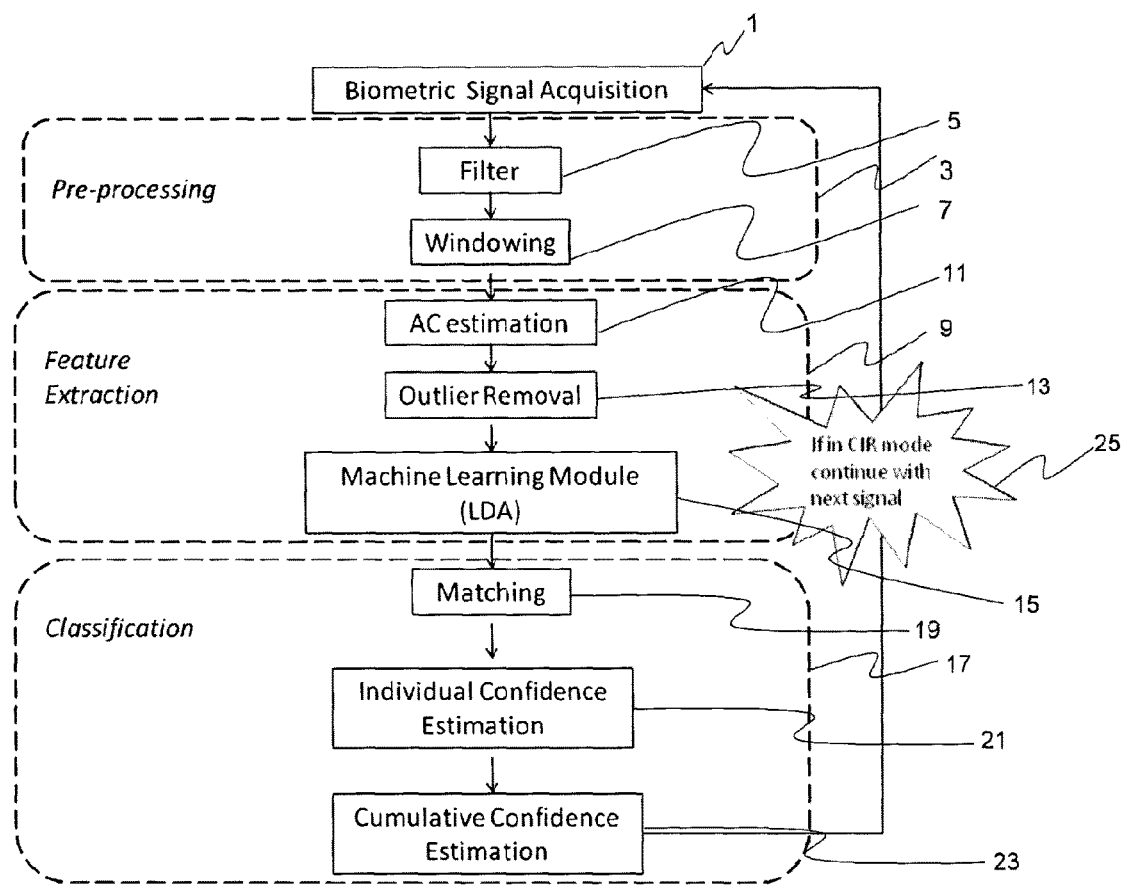
FIG. 1 is a workflow diagram illustrating the method for biometric processing of physiological signals.

In the drawings, embodiments of the invention are illustrated by way of example. It is to be expressly understood that the description and drawings are only for the purpose of illustration and as an aid to understanding, and are not intended as a definition of the limits of the invention.

DETAILED DESCRIPTION OF THE PREFERRED EMBODIMENT

The present invention is a biometric security system and method operable to authenticate one or more individuals using physiological signals. The method and system may comprises at least the modes of instantaneous identity recognition (IIR), and continuous identity recognition (CIR). The present invention concerns a complete approach, including a methodology and framework, to biometric recognition using physiological signals. Central to this invention is the utilization of a machine learning utility presented and adapted to the needs of different application environments which constitute different application frameworks. In addition the present invention incorporates a method and system for continuous authentication using physiological signals and a means of estimating relevant parameters.

Herein the following terms will be defined as follows: "feature extraction" refers to selecting time-invariant features from the biometric samples; "generic dataset" refers to biometric samples collected from a large number of anonymous individuals; "machine learning" refers to technologies, usually incorporating or implementing, learning of particular patterns and how to distinguishing them; "template design" may be an aspect of machine learning; and "physiological signals" refers to human bodily responses that are traditionally used in medical diagnostics but have been shown to exhibit subject-specific characteristics (examples: electrocardiogram (ECG), otoacoustic emissions (OAE), phonocardiogram (PPG), electroencephalogram (EEG), phtoplethysmogram (PPG), blood volume pressure (BVP) and other).

Additionally, the term "known and unknown enrollees" refers to the type of users for the provided biometric system. Known enrolees being users whose physiological signals are captured before execution of the machine learning and biometric signal processes. Unknown enrollees being users whose physiological signals cannot be practically known before the execution of the machine learning and biometric signal processes. This is because of continuous registrations and/or withdrawals from the biometric system during its operation (for example subway access systems).

Biometric recognition using physiological signals is a relatively new idea. Traditional prior art biometric systems use characteristics such as the face, the iris or the fingerprint in order to assess the identity of an individual. Despite the growth of the respective security sectors, traditional prior art biometric technologies fall short in addressing security issues in wide a range of application environments, such as welfare monitoring, tele-medicine, occupational welfare and other. The present invention is developed to overcome the short falls of the prior art.

The present invention incorporates physiological signal-based biometric methods and systems which provide more flexible solutions compared to traditional prior art biometric technologies. The present invention discusses applications in both access control (for example, such as physical or logical access control) and in remote monitoring (such as may be healthcare oriented or not). The present invention is a system and method whereby physiological signals can be captured for access control as well as on a continuous basis. An access control mode of the present invention may utilize physiological signals for the purpose of authenticating the identity of an individual in an instantaneous mode of operability. For example, access control may be utilized when only a short and fast reading of the signal from an individual is required in order to assess his/her identity. A continuous mode of the present invention may continuously and conveniently cause identity authentication of an individual to occur during long monitoring sessions.

The present invention may offer several advantages over known prior art systems and methods. The application of physiological biometrics generally offers advantages over prior known prior art, such as the resistance of biometric security systems and methods based on physiological biometrics to circumvention, replay and obfuscation attacks. More particularly, unlike the face or the iris, physiological signals are well protected inside the human body and are particularly difficult to forge, mimic or circumvent in any way. Furthermore, existing biometric or token-based identification methods are viewed as an inconvenience since the users need to actively interact with a biometric sensor or an ID apparatus in order to be identified. This is inconvenient or unworkable in situations where the user is under physical or mental stress such as soldiers in the field, healthcare patients, miners, etc. For example, it is impractical for a soldier to be identified with an iris camera during a field operation. Whereas, physiological signals can be collected via a wearable sensor without the direct engagement of the soldier. The reader should note that physiological signals are vital indications which are already monitored remotely in military operations. The opportunity of identifying the soldier using the same vital readings simply adds an authentication layer.

Furthermore, physiological biometrics offer the possibility of the biometric security system or method applying continuous authentication, as a fresh biometric reading may be undertaken every couple of seconds. Continuous authentication is an aspect of the present invention that is disclosed in more detail herein. Continuous authentication is not possible with traditional biometric modalities or other non-biometric identification technologies.

Some of the strengths and properties of biometric modalities, physiological (or medical) signals that represent advantages of the present invention over prior art that does not incorporate physiological signals include the following: (i) Universality—physiological signals satisfy the first and most prominent principle of biometrics, i.e., the universality criterion, since they are inherent, and can be collected from any living human; (ii) Permanence—many physiological responses are stable over a long period of time and even though specific local characteristics might change, the overall diacritical waves and morphologies are still observable; (iii) Uniqueness—while different signals may appear to conform to the same patterns, there is large inter-individual variability, resulting from different physiological parameters controlling the waveforms, and physiological factors (e.g., heart mass orientation, conductivity of various cardiac muscles, and cardiac activation order) can introduce significant variability among subjects (in fact, significant medical research had long sought to reduce this variability for universal diagnostic standards); (iv) Robustness to attacks—physiological signals are inherently immune to both attempts of credential falsification (i.e., circumvention using false signals), and of replay attacks (i.e., injection of a stolen biometric feature), and it is difficult to steal and re-use biological signals from others, as well as to adequately mimic the behavior of the organs which produce them, being the outcome of sympathetic and parasympathetic factors of the human body; (v) Liveness detection—physiological signals offer natural liveness detection, being only present in a living subject, but with medical biometrics, the recognizer can trivially ensure sensor liveness, this contrasts with other modalities whereby this capability requires significantly more resources; (vi) Continuous authentication—for monitoring applications, physiological signals offer continuous authentication of subject's identity, whereby a fresh reading every few seconds can be retrieved, as opposed to static fingerprint or iris images; (vii) Data minimization—for medical scenarios where physiological signals are inherently collected (e.g., for health diagnoses), their additional use for recognition purposes represents a useful synergy, that does not impose superfluous signal collection, i.e., data minimization is achieved.

Medical conditions are another challenging aspect of biometric recognition based on physiological signals and represent an advantage of the present invention over the prior art. Cardiac or other disorders, though not as frequent as injuries for more conventional biometrics, can limit the use of biometric systems using physiological signals. Disorders can range from an isolated irregularity, to severe conditions requiring medical assistance. Some local disorders (e.g., atria and ventricular premature contractions) can be handled with a specially designed detection mechanism. The present invention is operable to address medical conditions, whereas medical conditions pose a hurdle to prior art systems and methods.

Another advantage of the present invention over the prior art is that autocorrelation (AC) and machine learning utility Linear Discriminant Analysis (LDA) are important elements of the present invention, but the method and system of the present invention only partially depends upon AC and LDA. The LDA is deployed for different environments (e.g., frameworks such as small-scale, large-scale or distributed) in the present invention. In addition, the present invention may incorporate "Outlier Removal" functionality and the estimation of Individual and Cumulative confidences. These aspects of the present invention distinguish it from the prior art and cause the present invention to be more efficient and effective than the prior art.

Yet another advantage of the present invention over the prior art is that the method and system of the present invention does not encompass signal validation steps. Known prior art incorporates signal validation steps.

The biometric recognition system and method of the present invention may use physiological signals to operate in any of the following two modes; Instantaneous Identity Recognition (IIR); and Continuous Identity Recognition (CIR).

The IIR mode is operable to provide physical or logical access to protected environments. A short reading (for example, such as up to a few seconds) of the physiological signal is acquired from the individual and used for biometric matching against already enrolled biometric templates. Upon a successful match, the user is granted access to the physical or logical environment. A skilled reader will recognize that different forms of hardware of biometric systems and methods can operate under the IIR mode. For example, the recognizer can be a wall or ground-mounted device at a checkpoint that a user needs to cross before physically entering a restricted area. Alternatively, portable electronic devices, such as smart-phones, PDAs, medical or gaming devices and other may conduct biometric recognition with physiological signals in the IIR mode.

The CIR mode is operable with physiological signals to identify an individual over a period of time, so that the physiological signals of an individual are accessed continuously during a long monitoring session. Examples of application environments for the CIR mode include military environments, emergency services, civilian field workers (e.g. miners), healthcare, sports, etc. During the CIR mode of operation, the identity of an individual is assessed multiple times. This is done by collecting a new reading of the physiological signal at multiple intervals, for example, such as every couple of seconds, and by using the readings to perform biometric matching. Each distinct biometric decision that is made during the session is independent. In some embodiments of the present invention, consecutive biometric decisions may be aggregated to achieve an estimation of an overall recognition confidence during the monitoring session.

The IIR mode includes the steps of enrolment and biometric recognition. The enrolment step of the IIR mode may be operable to achieve identity recognition (for example, such as identification or verification) of an individual against a biometric template.

Enrolment may involve at least one individual initiating the capture of at least one physiological signal on an electronic device. The electronic device may be network-connected or not network-connected, and any connection may be wired or wireless. The physiological signal may be biometrically processed with a machine learning utility that may be incorporated: in the electronic device; on a central server linked to or otherwise connected to the electronic device either through a wired or wireless connection (for example, such as in Software as a Service (SaaS)), or incorporated in another remote device that is linked or otherwise connected to the electronic device either through a wired or wireless connection.

If the machine learning utility is incorporated in a central server, a secure communication session may be established between the network-connected electronic device and a remote server linked or linkable to the network-connected device. The physiological signal may be communicated to the remote server. The remote server may biometrically process the physiological signal with the machine learning utility operable so that the recognizer may learn the variability of the physiological signals in the relevant population. In response to the communication of the physiological signal, the remote server may be operable to communicate a personal transformation rule or a biometric template to the network-connected electronic device.

The step of biometric recognition of the IIR mode may involve identification or verification of the identity of an individual. During this step, at least one individual may initiate the capture of at least one physiological signal on an electronic device. The aim of this step is to authenticate the identity of the individual. The physiological signal may be biometrically processed with a signal processing method or system of the electronic device, or with a signal processing method or system incorporated in a central server, for example, such as a SaaS, or with a signal processing method or system of another device that is linked to or otherwise connected to the electronic device either through a wired or wireless connection.

If the signal process method or system is incorporated in the central server, the signal may be communicated to the sever with a secure communication session whereby the server responds with a biometrically processed physiological signal. The biometrically processed physiological signal may be generated by a machine learning enabled method or system.

To achieve identification of an individual the biometrically processed physiological signal may be matched against a database of enrolled biometric templates that includes biometric templates captured from multiple individuals. The database and the matching operation may exist and occur either on the electronic device or on the remote central server. If the database and the matching operation exist and occur on the remote central server, the identity information may be communicated back to the electronic device.

A verification step may be incorporated in the present invention. To achieve verification an identity claim may be initiated by the user by name, password, device ID number, or any other non-biometric manner. The electronic device, or the remote server, may match the biometrically processed physiological signal against the biometric template corresponding to the claimed enrolled individual.

To indicate whether an individual has been identified and/or verified, an "accept" or "reject" decision may be communicated either from the electronic device, or to the electronic device by the remote server and then from the electronic device.

The CIR mode includes the steps of enrolment and biometric recognition. The enrolment step of the CIR mode may be operable to achieve identity recognition (for example, such as identification or verification) of an individual against a biometric template. The enrolment step of the CIR mode functions in a manner similar to that described herein for the IIR mode.

The biometric recognition step of the CIR mode may achieve either identification or verification of the identity of an individual. During this step, at least one individual may initiate a biometric authentication session by the capture of at least one physiological signal on an electronic device. During the session, the individual may be continuously recognized, for example, such as identified or verified, via a capture of the physiological signal of the individual on an electronic device occurring at intervals or continuously during the session. Every individually captured instance of the physiological signal may result in an identity assessment. The identity assessment may undertake a procedure similar to that described for the IIR biometric recognition step.

Biometric recognition may be performed locally on the electronic device or centrally on a remote server in a SaaS fashion. Identification or verification decisions throughout the biometric authentication session are accumulated for the estimation of an overall system threat level. When a variation is observed between a biometrically processed physiological signal and a biometric template, the template is re-estimated (via an automatic enrolment operation) or enhanced with new information.

The present invention may be designed and implemented in two possible implementations—a small-scale recognition framework or a large-scale recognition framework.

The small-scale recognition framework implementation of the present invention may be utilized for applications involving a small number of known enrollee individuals. The small-scale recognition framework implementation of the present invention may include an access system that is either central or distributed.

A central access system for a small-scale recognition framework implementation of the present invention may store the enrollee individual's biometric templates centrally on a remote server. The electronic devices that capture the physiological signals may be network-connected and may be connected by a wired or wireless connection. The machine learning method to biometric signal processing may be operable so that the recognizer may learn the variability of the relevant population and may include in some embodiments a generic dataset.

A distributed system for a small-scale recognition framework implementation of the present invention may involve every user having an electronic device that is enabled with biometric authentication method or system operable to use physiological signals. The electronic device may be personalized by securely storing on it the biometric template of the respective individual user. The personalized electronic device may be network-connected and may be connected by a wired or wireless connection, or may not be network-connected. The machine learning method or system for biometric signal processing may be operable so that the recognizer may learn the variability of the relevant population and may include in some embodiments a generic dataset.

A large-scale recognition framework of the present invention may be utilized for applications involving a large number of unknown individual enrollees. The large-scale recognition framework implementation of the present invention may include an access system that is either central or distributed.

A central access system of a large-scale recognition framework implementation of the present invention may be similar to the small-scale access implementation in that the enrollee individual's biometric templates may be stored centrally on a remote server and the electronic devices that capture the physiological signals may be network-connected and may be connected by a wired or wireless connection. The machine learning method or system for biometric signal processing may enable the recognizer to learn a generic dataset.

A distributed access system of a large-scale recognition framework implementation of the present invention may be similar to the small-scale access implementation in that every user may have an electronic device that is enabled with a biometric authentication that uses physiological signals. The electronic device may be personalized by securely storing on it the biometric template of the respective individual user. In addition, a personal transformation rule may be stored on the device and used for biometric recognition. The personal transformation rule may be estimated using a machine learning method which enables the recognizer to learn the variability of the particular individual user and a generic dataset.

Embodiments of the present invention may be configured to utilize one or more physiological signals. If more than one physiological signal is utilized the present invention may be deployed in a multi-modal framework. For example, a multi-modal framework may be a system or method whereby more than one physiological signal is collected and the signals may be combined by the recognizer. A multi-modal framework may provide additional information to the recognizer. The additional information may cause the present invention to achieve biometric performance benefits.

In a multi-modal framework physiological signals that may be collected and combined include signals that are: (i) of the same bodily origin, for example, such as cardiovascular such as ECG, BVP, PCG, and/or PPG; (ii) of the same electrophysiological origin, for example, such as ECG Lead I, Lead II and/or Lead III; and/or (iii) of completely different bodily origin, for example, such as ECG, EEG, and/or OAE.

A skilled reader will recognize that the specific function of the combination means whereby physiological signals may be combined may depend on the type of signals that are to be combined. For example, a combination means may perform a combination at a raw-data level, feature level, or decision (or score) level.

The present invention may include machine learning steps that are incorporated in a novel and innovative manner. Such machine learning steps may provide more flexible and effective deployment of authentication using physiological signals, with improved performance characteristics when compared to the prior art. More particularly, the present invention may provide a method and system operable to use machine learning to learn the variability of the physiological signals in the relevant population.

It should be understood that the present invention involves an approach to biometric templates that incorporates machine learning in a manner that provides protection against attacks. For example, the present invention may ward against attacks such as an attack by an intruder attempting to use his or her biometric signal or signals to gain unauthorized access to the biometric security system of the present invention.

A skilled reader will recognize that a variety of physiological signal acquisition apparatuses and devices may be utilized by an incorporated in the present invention. Such apparatuses and devices may have variant requirements for sensor orientation. As an example, the following provides possible apparatuses and devices to be utilized to collect physiological signals from particular body locations: (i) apparatuses or devices for sensing physiological signals of the wrist/arm may include ECG, BVP; (ii) finger-touch surface sensors used as apparatuses or devices may include ECG (fingers from both hands), or PPG (one finger); (iii) ECG chest sensor (such as a wearable belt around the chest or sensor-patch that sticks on the body); (iv) apparatuses or devices for sensing physiological signals from an ear may include PPG, or OAE; (v) for ECG generally any other sensor orientation can be deployed as long as two-reference points across the heart are used.

Enrollment Procedure

The purpose of the enrollment procedure of the present invention is the registration with a biometric system and the design of a unique biometric template for every enrollee individual.

Several aspects of the enrollment procedure relate to the application framework of the present invention. Generally, during enrollment at least one individual initiates the capture of at least one physiological signal on an electronic device which in some embodiments can be network-connected by way of either a wired or wireless connection. The electronic device may also not be network-connected in some embodiments of the present invention.

The physiological signal is biometrically processed with a machine learning utility on any of: the electronic device; a central server, for example, such as in a Software as a Service (SaaS) fashion; or any other device that may be connected or otherwise linked to the electronic device through a wired or wireless connection.

In an embodiment of the present invention that incorporates a central server, a secure communication session is established between the network-connected electronic device and a remote server linked or linkable to the network-connected device. The physiological signal is communicated to the remote server. The remote server biometrically processes the physiological signal with the previously described method which encompasses a machine learning utility which enables the recognizer to learn the variability of the physiological signals in the relevant population. In response to the communication of the physiological signal, the remote server is operable to communicate a personal transformation rule or a biometric template to the network-connected electronic device. The above procedure enables identity recognition (for example, such as identification or verification) of the individual against the biometric template.

Recognition Procedure

The purpose of the recognition procedure (for example, such as identification or verification) of the present invention is the establishment of the identity of an individual.

During this step, at least one individual initiates the capture of at least one physiological signal on an electronic device with the aim of authenticating his/her identity. The physiological signal is biometrically processed with a signal processing method on the electronic device (as shown in FIG. 6), or on a central server in a SaaS mode (as shown in FIG. 7).

Figure 6:
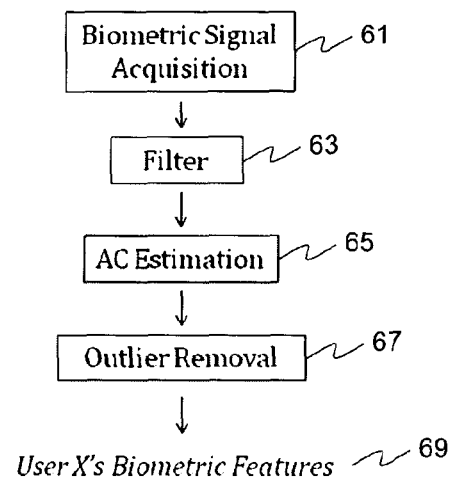
FIG. 6 is a workflow diagram illustrating the steps for the estimation of biometric features on a personal device within a distributed framework.

The signal processing method on the electronic device, as shown in FIG. 6, may include a set of steps. For example, a biometric signal, being a physiological signal, may be acquired 61. The signal may be filtered 63. An AC estimation 65 may be undertaken, and outlier removal 67 may be performed subsequently. The result of these may be the identification of a user's biometric features 69.

Figure 7:
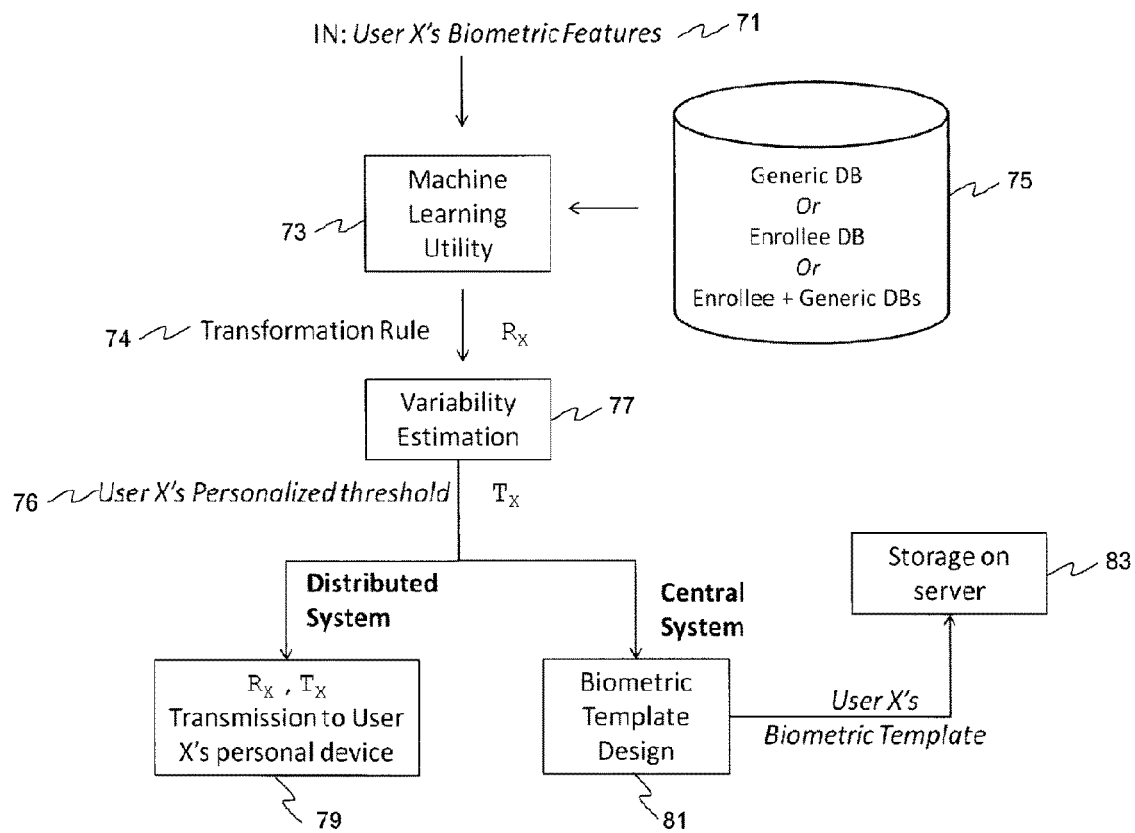
FIG. 7 illustrates the enrollment workflow at the server (within a central or distributed setup).

As shown in FIG. 7, an embodiment of a system of the present invention may utilize a user's biometric features as input 71. A machine learning utility 73 may process the features. A database 75, for example, such as a generic database, an enrollee database, or an enrollee and generic database, may be linked or otherwise connected to the machine learning utility, and information may be transferred from the database to the machine learning utility. A transformation rule 74 may be applied to the output of the machine learning utility to produce an result, for example, such as Rx, before the output is transferred to the variability estimation means 77. The user's personalized threshold 76 may be applied to the output of the variability estimation to produce a result, for example, such as Tx. In an embodiment of the present invention that incorporates a distributed system, the Rx and Tx results may be transferred to a user's personal device 79. In an embodiment of the present invention that incorporates a centralized system a biometric template design means 81 may be utilized to create a user's biometric template that may be stored on a server 83.

If a central server is incorporated in the present invention, the physiological signal is communicated to the sever with a secure communication session whereby the server responds with a biometrically processed (for example, such as with a machine learning enabled method) physiological signal. For "identification", the biometrically processed physiological signal is matched against a database of enrolled biometric templates from different individuals. This database and the matching operation can take place on: the electronic device; the remote central server; or on another device that is linked or otherwise connected to the electronic device by a wired or wireless connection.

If a central server of the present invention is utilized to store the database and the matching operation, the identity information is communicated back to the electronic device.

For "verification", an identity claim is initiated by the user by name, password, device ID number or any other non-biometric fashion. The electronic device or the remote server matches the biometrically processed physiological signal against the biometric template corresponding to the claimed enrollee. An "accept" or "reject" decision is communicated to the electronic device by the remote server.

Physiological Signal Processing Method for Biometric Recognition

The pattern recognition for biometrics using physiological signals depends upon the quality of the employed feature extractor. The present invention comprises a method and system that utilize feature extraction methods that are fiducial independent. (Fiducial points are specific points of interest on a physiological signal.) Fiducial based feature extraction methods may permit localized approaches, whereas non-fiducial algorithms are operable for holistic approaches. As embodiments of the present invention may involve a non-fiducial algorithm such embodiments may therefore be directed to holistic approaches.

The present invention further provides a benefit over the prior art in that fiducial based approaches require perfect localization of the points of interest. This increases the overall complexity and risks precision, because there is no universally acknowledged rule to guide this process. In other words, the variability of healthy waveforms is sufficiently high, so that there is no common basis for the localization of these points. Subsequently, these solutions may require subjects to be recorded for longer periods of time, until exemplary heart beats are collected. Thus, the present invention, that does not apply fiducial based approaches, may be less complex, and more effective under typical clinical irregularities (for example, such as premature heart beats for cardiovascular physiological signals), while fiducial based prior art approaches are generally more complex and ineffective under typical clinical irregularities. The holistic approach of the present invention incorporates a discriminant analysis of autocorrelated (AC) signals.

The method for physiological signal processing for biometric recognition may encompass three steps including: (1) pre-processing; (2) feature extraction; and (3) classification. A block diagram of the physiological signal processing method is shown in FIG. 1. Prior to any of the three steps occurring, a bio-metric physiological signal may be acquired 1, for example, such as by a bio-metric signal acquisition means.

Preprocessing. Once a bio-metric physiological signal is acquired, a pre-processing step 3 may be undertaken. Biometric processing of physiological signals may involve noise removal. The signals may be filtered 5 in a manner that is appropriate to remove high and low frequency noise. A skilled reader will recognize the variety of appropriate manners, modes and methods that may be utilized to remove high and low frequency noise. For example, an appropriate manner of removing high and low frequency noise for several physiological signals may be the use of a Butterworth band-pass filter. The cutoffs of the filters may be set according to the properties of the signal (for example, such as 1 Hz-40 Hz for ECG). A skilled reader will recognize that other appropriate manners of removing high and low frequency noise may also be applied in the present invention.

In order to augment the available information and enhance the biometric performance segment of a physiological signal, said signal may be subsequently subjected to windowing 7. The process of windowing involves a process whereby, given a particular segment of a signal, a number of smaller windows can be acquired using a sliding window with a pre-determined level or overlap. A skilled reader will recognize that this level may be determined according to the needs of the application environment. As an example, if a 6 second segment of physiological signal is available, the windows may overlap by 1 second or less.

Figure 3:
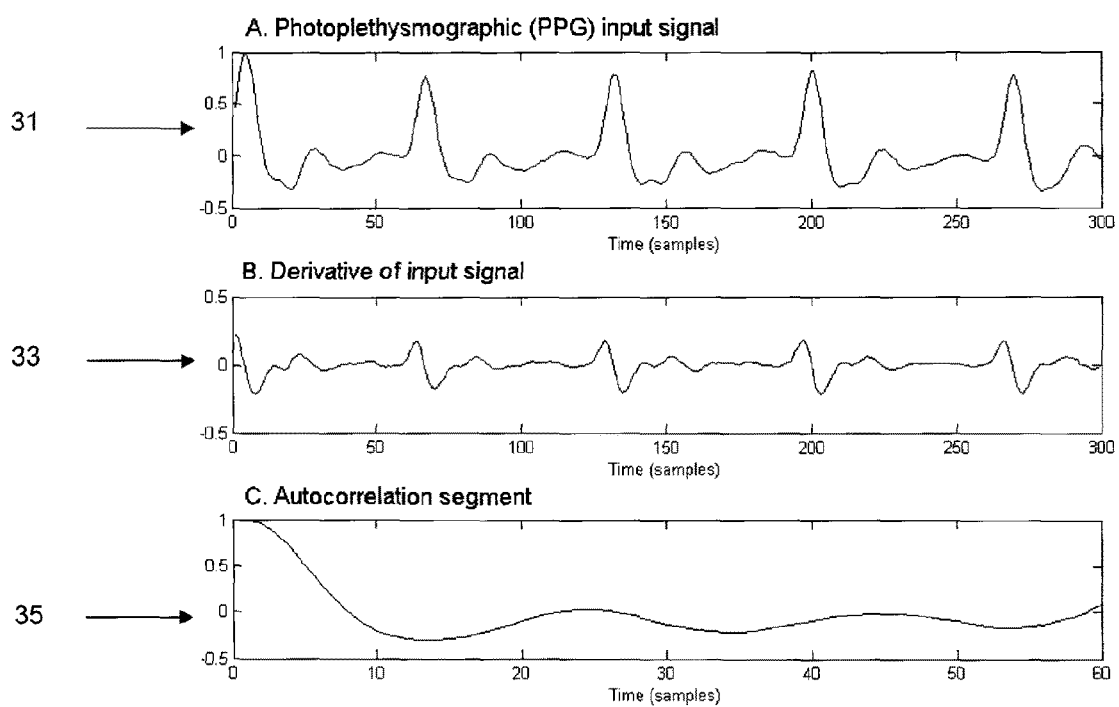
FIG. 3 illustrates the analysis of a photoplethysmographic (PPG) signal with the disclosed method for biometric signal processing of physiological signals.

A skilled reader will recognize that certain physiological signals may require further preprocessing prior to feature extraction. As an example, in one embodiment of the present invention an estimation of the derivative of a photoplethysmographic (PPG) signal may be applied, as shown in FIG. 3. This operation may be performed for each of the isolated PPG windows. For example, a PPG input signal 31 is shown in FIG. 3, as is an estimation of the derivative of a PPG input signal 33 that may be undertaken by the present invention.

Feature Extraction. After pre-processing is completed the present invention may undertake feature extraction 9. While various approaches, means and methods may be utilized to achieve feature extraction, a computationally efficient option that may be applied in embodiments of the present invention is the autocorrelation (AC). The AC may involve AC estimation 11. The AC is computed and normalized for all windows acquired from the previous operation using:

$$\hat{R}_{xx}[m] = \sum_{i=0}^{N-|m|-1} x[i]x[i+m] \quad (1)$$

Where x[i] is the windowed signal for i=0, 1 . . . (N−|m|−1), x[i+m] is the time shifted version of the windowed signal with time lag of m=0, 1 . . . (M−1); M<<N and N is the length of the windowed signal. Out of Rxx only a segment is retained for further processing.

Figure 2:
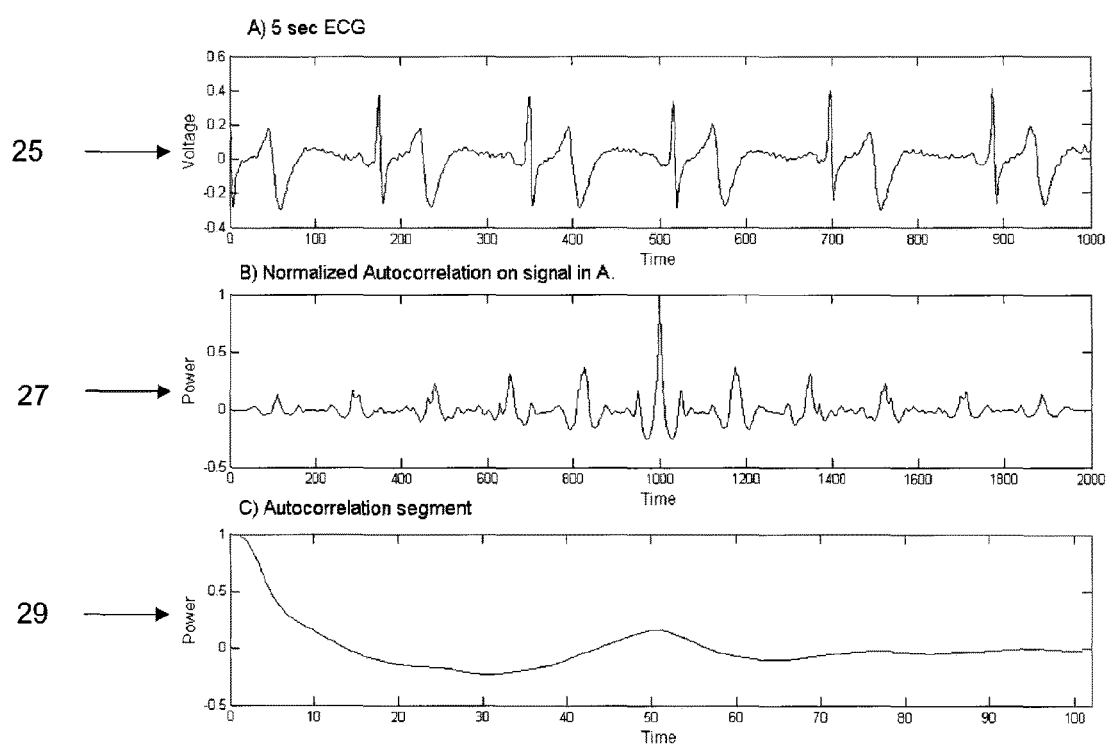
FIG. 2 illustrates the analysis of an electrocardiogram (ECG) signal with the disclosed method for biometric signal processing of physiological signals.

An example of this analysis for an AC segment 35 is shown in FIG. 3., and other examples for a normalized AC on a 5 second ECG 27 and an AC segment 29 are shown in FIG. 2. An example of this analysis for a 5 second ECG 25 is shown in FIG. 2.

Following the estimation of the AC for every window of the physiological signal, outlier windows may be detected and discarded 13, as shown in FIG. 1.

Figure 4:
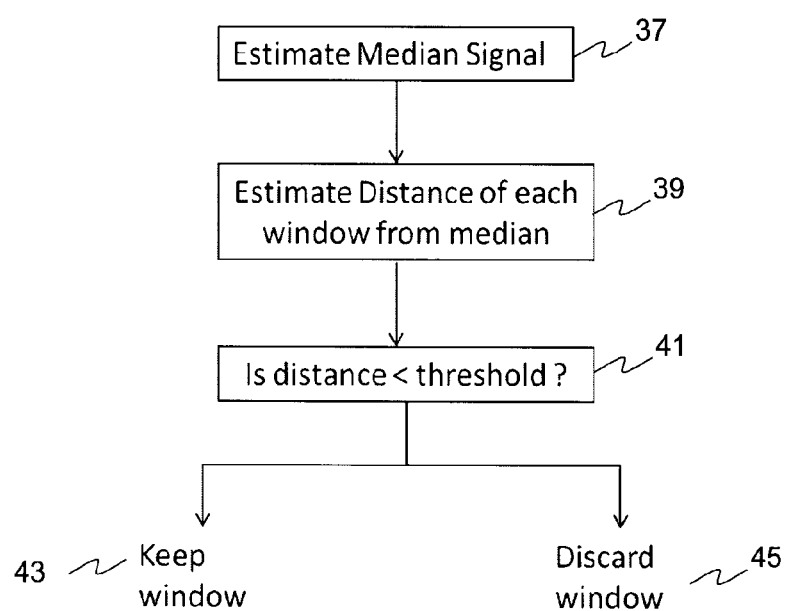
FIG. 4 illustrates the workflow for discarding outlier segments of the physiological signal.

As shown in FIG. 4, a procedure for outlier windows may involve the median of all windows being estimated 37, for example, such as with sorting or selection algorithms, or by way of statistical modeling. The median is used as an average descriptor of the windows and their dissimilarity that allows the present invention to classify certain windows as outlier windows. The distance, for example, such as the Euclidean or other distance, between the median and each window is computed by the present invention 39. The distance may be compared to the threshold 41. If the distance is bigger than a threshold the window may be excluded from all subsequent analyses as an outlier 45. Or, if the distance is not bigger than a threshold the window may be kept 43.

The present invention may incorporate a method and framework for practical implementation of the Linear Discriminant Analysis (LDA) machine learning utility in distributed systems, as is discussed in J. Gao, F. Agrafioti, H. Mohammadzade, D. Hatzinakos, "ECG for Blind verification in Distributed Systems", *Int. Conf. on Acoustics, Speech and Signal Processing*, p.p. 1916-1919, 2011.

Linear Discriminant Analysis (LDA) is applied on the AC segment. LDA is well-known supervised machine learning technique that manages to reduce the dimensionality of the feature vectors while making classes more distinguishable. Given a training set $\{z_i\}_{i=1}^U$, z containing U classes with each class $Z_i = \{Z_{ij}\}_{j=1}^{U_i}$ containing number of autocorrelated windows $Z_{ij}$ a set of K feature basis vectors $\{\psi_m\}_{m=1}^k$ can be estimated by maximizing Fisher's ratio. Maximizing this ratio is equivalent to solving the following eigenvalue problem:

$$\psi = \arg\max_{\psi} \frac{|\psi^T S_b \psi|}{|\psi^T S_w \psi|} \quad (2)$$

where $\psi=[\psi_1, \ldots, \psi k]$, and Sb and $S_w$ are the between and within class scatter matrices respectively. LDA finds $\psi$ as the K most significant eigenvectors of $(S_w)^{-1}S_b$ which correspond to the first K largest eigenvalues. A test input window z undergoes the linear projection $y=\psi^T z$ prior to classification.

Classification. Classification 17 may be applied by the present invention, as shown in FIG. 1. A skilled reader will recognize that various approaches to classification may be utilized by the present invention. For example, one embodiment of the present invention may apply a simple solution, whereby classification is performed using the nearest neighbor classifier and the Euclidean distance as the similarity measure.

As shown in FIG. 1, one embodiment of the present invention may involve matching 19, individual confidence estimation 21 and cumulative confidence estimation 23 in a classification step 17.

Moreover, once a classification step is completed an embodiment of the present invention that involves a CIR mode may continue with the next signal 25, and repeat the pre-processing 3, feature extraction 9 and classification 17 steps.

Individual Biometric Confidence

In embodiments of the present invention a biometric decision may be associated with a confidence in the present invention. Multiple instances of the biometric modality, from multiple people, are required to accurately estimate this confidence. These instances of biometric modality are used to estimate the expected intra-class and inter-class distances so that a new input is allocated accordingly to a prior probability. When the system operates under the verification mode of operation, the confidence is associated with the "accept" or "reject" decisions. When in the CIR mode of operation, the individual confidence is independently estimated for every for every biometric decision that is made (for example, such as for every reading ph the physiological that is acquired within a monitoring session).

Intrusion may be suspected by the present invention in any of the following situations: (i) Alarm Type I: Identity Rejection with high individual confidence; and (ii) Alarm Type II: Identity Acceptance with significantly low individual confidence (suspicious acceptance), as this case raises suspicions for false acceptance.

Cumulative Biometric Confidence

When the present invention is operating in the CIR mode, the Cumulative Biometric Confidence is also estimated. This is done by assessing the progression of the biometric decisions in reference to time. For example, the cumulative confidence of an alarm output increases as more rejections (of high individual confidence) or suspicious acceptances become available.

In the present invention, when an alarm occurs the Cumulative Biometric Confidence increases. This initializes a period of suspected intrusion monitoring, during which the cumulative confidence will either increase or remain at a previous level.

The intrusion monitoring period differs between Alarm types I and II. In both cases, the cumulative confidence may reach 100% within a predetermined number of readings of the physiological signal. Examples of intrusion monitoring for Alarm types I and II are provided in the table below.

|  | Alarm Type I | Alarm Type II |
|---|---|---|
| Initial Biometric Decision | Reject of high individual confidence | Accept of very low individual confidence |
| Possible cause | Case 1: Rejection of an Illegitimate claim | Case 1: False acceptance of an illegitimate claim |
|  | Case 2: Rejection of a legitimate claim due noisy signal | Case 2: Poor acceptance of a legitimate claim due to noisy signals. |
| Intruder monitoring period | Fixed number of verification periods (e.g. 3 × 20 seconds) | Fixed number of verification periods (e.g. 5 × 20 seconds) |
| Expected outcome | Case 1: Cumulative confidence will reach 100% within a number of readings of the physiological signal. | Case 1: Cumulative confidence will reach 100% within a number of readings of the physiological signal. |
|  | Case 2: Cumulative confidence will not change. | Case 2: Cumulative confidence will not change. |

Figure 5:
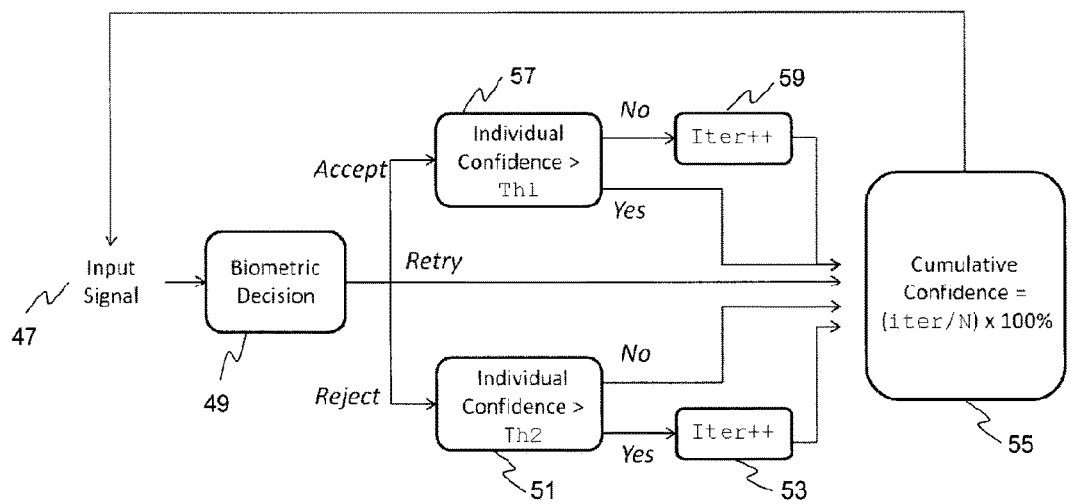
FIG. 5 is a workflow diagram illustrating the cumulative biometric confidence estimation.

In the CIR mode of operation of the present invention, cumulative biometric confidence is estimated by accumulating biometric decisions and the associated individual confidences. An example of a workflow for the estimation of the overall threat level is shown in FIG. 5. An input signal 47 is provided to a biometric decision means 49. Two thresholds are defined on the confidence, depending on whether the biometric decision at a particular instance was "accept" or "reject". For example, Th1 is chosen according to the intra-class distance distribution, and Th2 is chosen according to the inter-class distribution for the particular physiological signal. Generally, thresholds Th1 and Th2 may relate to an intra-subject variability.

An evaluation as to whether individual confidence is greater than Th1 57 may be undertaken and should individual confidence not be greater than Th1 an Iter++ step 59 may be undertaken, and no Iter++ step may be undertaken if individual confidence is greater than Th1. (In this embodiment of the present invention inter is the current iteration of the process, and at an initialization point iter will equal zero.) A similar analysis may be performed to determine if individual confidence is greater than Th2 59 and if individual confidence is greater than Th2 an Iter++ step 53 may be performed. If individual confidence is not greater than Th2 no Iter++ step may be performed. All analysis output may be transferred to a cumulative confidence algorithm or calculation step 55, whereby a cumulative confidence is equal to (iter/N)×100%, wherein N is the total number of physiological signal readings until cumulative confidence can reach 100%. The output of the algorithm or calculation step 55 may be provided as an input signal and the steps shown in FIG. 5 may be repeated.

Examples of Biometric Confidence

The cumulative biometric confidence of the present invention and its benefits can be better understood through an example. A skilled reader will recognize that this example is provided solely to enhance the description of the present invention and that other embodiments of the present invention other than that described in the example are also possible.

Should the present invention be implemented for a welfare monitoring session of military agents in the field, every soldier may be equipped with a portable and wearable electronic device which collects and monitors vital signals. In this example, the ECG signal is wirelessly transmitted to a central monitoring station, where personnel are supervising operations. At intervals, for example, such as every couple of seconds, the ECG signal of every agent is matched against a database of enrollee individuals for the purpose of identifying the agent as a specific person.

A common problem with wearable devices is that a sudden movement or dislocation may generate noise. The noise can potentially affect the accuracy of the biometric recognition. For example, an agent may move the recording equipment while adjusting his or her uniform. The signal that is recorded during that period is likely to be rejected by the biometric recognition system or method with high individual confidence. This instance fits within the category of an Alarm Type I. For the monitoring personnel it may be interpreted as a warning signal of intrusion (for example, it may warn that the agent and the device may be compromised). In the present invention such an instance of false rejection is accompanied by the Cumulative Biometric Confidence. Despite the alarm and its warning of intrusion, the cumulative confidence can provide a clear indication of whether such an alarm is false or not. Therefore in an implementation of the present invention isolated events, such as device movement, do not increase the Cumulative Confidence of the alarm over time.

Frameworks for Physiological Biometric Recognition

The present invention may be implemented in a small-scale recognition framework or a large-scale recognition framework for the purpose of biometric signal processing for physiological signals. The descriptions of the frameworks provided herein are directly related to real life application settings, and the systems and methods of the present invention that are described herein address the fundamental challenges of such environments.

Small-scale Recognition Frameworks

Small-scale recognition frameworks include security systems that are used by a small and known population of individuals. For example, in present invention systems and methods for small-scale recognition frameworks the biometric templates of all enrollee individuals are known before the system is set to operate. This type of system is useful for example for enabling access control in a company, identity management for patients of particular clinic, or continuous identity validation for field agents (for example, such as police officers, fire-fighters, soldiers, and pilots). Within a small scale framework, recognition is performed either: (i) centrally on a server; or (ii) locally on an electronic device where the biometric templates are a saved. Such systems can operate under the CIR or IIR modes of the present invention.

In small-scale applications of the present invention, the individuals to be recognized are known a priori, and such applications may have several uses, such as for access control in companies, continuous authentication of personnel in a monitoring setting, etc. The variability of the physiological signal among the relative population is learned by the present invention by training the machine learning algorithms on recordings from the particular enrollee individuals.

Figure 8:
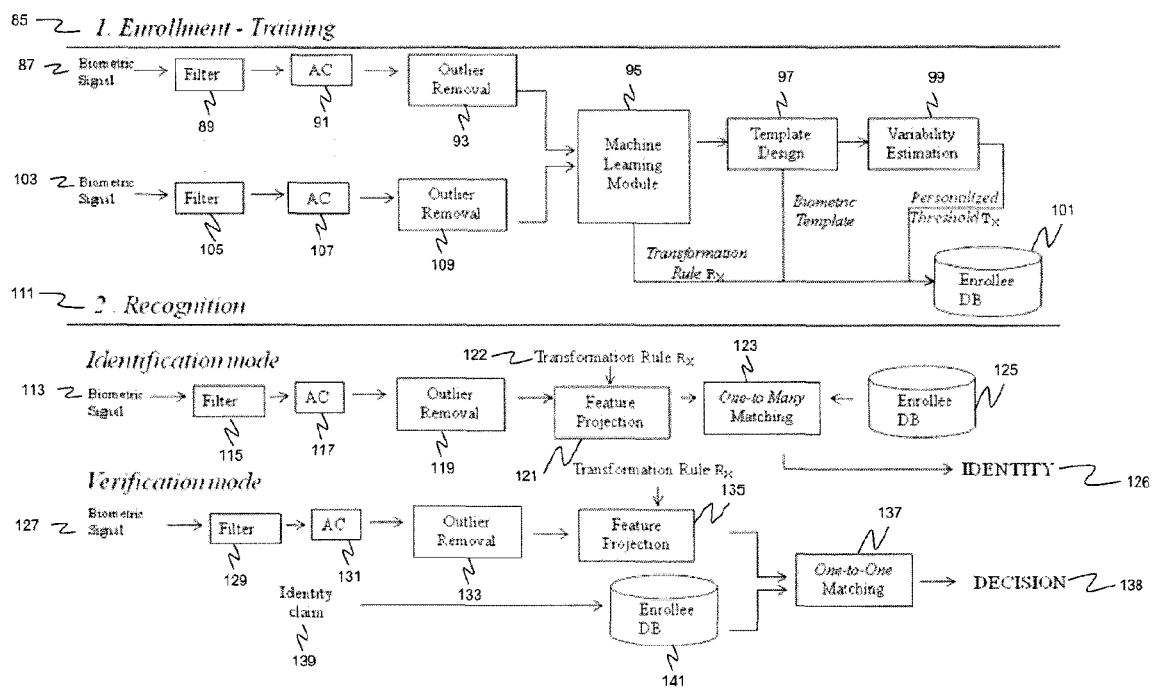
FIG. 8 is a system diagram illustrating a small scale recognition framework in accordance with the present invention.

An example of a small-scale application of the present invention is shown in FIG. 8. In an enrollment training mode 85 a biometric signal 87, such as a physiological signal, is processed in sequential order by a filter module 89, an AC module 91 and an outlier removal module 93. The result of this processing is transferred to a machine learning module 95. Embodiments of the present invention may be operable to process multiple biometric signals. As shown in FIG. 8, an additional second biometric signal 103, such as a physiological signal, may be processed in sequential order by a second filter module 105, a second AC module 107 and a second outlier removal module 109. The result of this processing of a second biometric signal is transferred to the machine learning module. A skilled reader will recognize that additional processing modules may be incorporated in the present invention process multiple biometric signals.

The results of the processing of the one or more biometric signals transferred to the machine learning module may be processed in sequential order by a template design module 97 and a variability estimation module 99. The result of the variability estimation module may be a personalized threshold, for example as may be represented as Tx, that is transferred to an enrollee database 101. A transformation rule, for example as may be represented as Rx, may be transferred from the machine learning module to the enrollee database 101. A biometric template may be transferred from the template design module to the enrollee database. All information or other data transferred to the enrollee database may be stored in the database, and the database may be local to or remote from the system.

In a recognition mode 111 of the embodiment of a small-scale application of the present invention, as shown in FIG. 8, an identification mode may involve an identification biometric signal 113, such as a physiological signal, being processed in sequential order by an identification filter module 115, an identification AC module 117, an identification outlier removal module 119, and an identification feature projection module 121. The identification feature projection module may further receive an identification transformation rule 122, such as may be represented as Rx, as input for use in the processing and operation of the identification feature projection module. The result from the identification feature projection module may be transferred to an identification one-to-many matching module 123 that may receive input from an identification enrollee database 125. The identification one-to-many matching module may output the identity 126 of a user related to the identification biometric signal 113.

The recognition mode 111 may incorporate a verification mode that may involve a verification biometric signal 127, such as a physiological signal, being processed in sequential order by a verification filter module 129, a verification AC module 131, a verification outlier removal module 133, and a verification feature projection module 135. The verification feature projection module may further receive a verification transformation rule 134, such as may be represented as Rx, as input for use in the processing and operation of the verification feature projection module. The result from the verification feature projection module may be transferred to a verification one-to-one matching module 137. An identity claim 139, for example, such as a password or other identity representation, may be transferred to a verification enrollee database 141. Data from the verification enrollee database pertaining to the identity claim may be transferred to the verification one-to-one matching module 137. The verification one-to-one matching module may output a decision 138 as to whether the identity claim matches the verification biometric signal.

A small-scale recognition system and method of the present invention may be either central or distributed. In an embodiment of the present invention that is central the enrollee individual's biometric templates are stored centrally on a remote server. The electronic devices that capture the physiological signals are network-connected and may be wired or wirelessly connected. The machine learning method to biometric signal processing enables the recognizer to learn the variability of the relevant population and may include a generic dataset. The learning operation may be controlled by, and on, the server, after the physiological signals are communicated to the server.

In an embodiment of the present invention that is distributed every user may hold an electronic device that is enabled with biometric authentication using physiological signals. The electronic device is personalized by securely storing on it the biometric template of the respective user. The personalized electronic device can be network-connected by a wired or wireless connection, or not network-connected. The machine learning method for biometric signal processing may be operable so the recognizer may learn the variability of the relevant population and may include a generic dataset. The learning operation may take place on the electronic device or on the server.

A small-scale recognition system or method embodiment of the present invention, may include some general aspects. For example, during enrollment (which may be used for training as well in implementation of the present invention), a reading of the signal is acquired from every individual (for example, such as from every employee of a company) and is subjected to feature extraction. The features of all individuals are used as input into a machine learning utility (for example, such as a learning algorithm). The machine learning utility, or learning algorithm, is operable to generate: (i) a biometric template for each enrollee; and (ii) a transformation rule that will guide both first decisions and then a verification mode of the present invention. The small-scale recognition system or method of the present invention may be understood as including a first enrollment training workflow and a second recognition workflow.

The small-scale recognition system or method embodiment of the present invention incorporates an identification mode and the verification mode. The identification mode consists of one or more one-to-many matches (for example, such as for identifying a particular individual), and the verification mode consists of a one-to-one match for verifying the identified individual. The identification mode and the verification mode may be implemented using a recognizer component, said component being either a layer or a utility.

The following is an example of the application of the small-scale access application of the present invention, implemented for use in connection with a company access system. A skilled reader will recognize that this is provided merely for the purpose of providing an example of one embodiment and implementation of the present invention and that other embodiments and implementation of the present invention are possible.

In this example of an embodiment of the present invention, a company may invite its employees to a signal collection session, and a biometric sample may be acquired from every employee. Each employee would therefore be an enrollee individual. The machine learning utility of the system may be trained offline to "learn" the biometric morphologies of the particular employees. The system may be used for physical access control for examples for purposes of identification and verification.

Identification: When an employee requests access to particular facility, a new sample of the physiological signal may be collected, and matched against the database that is stored centrally, by operation of a recognizer component for example. The answer of the recognizer can be one of the following three answers: 1. The identity information of the employee (answering the question "Who is this employee?"); 2. The clearance level of the particular employee. 3. A Yes/No response equivalent to a watch-list search (answering the question "Is this person an employee?" rather than "Who is this employee?").

Verification: An employee requests access to a facility and at the same time presents credentials that make an identity claim (for example a name badge, ID card, etc.). A sample of the physiological signal is collected and compared against the biometric template that corresponds to the claimed identity. The system replies with a YES/NO answer.

As another example of an implementation of an embodiment of the present invention, when a newborn is delivered an OAE signal may be collected and stored in a central database. The machine learning utility may re-learn when new babies are enrolled. If identity is questioned, a new sample of the medical signal is collected and used for biometric matching with the following possible outcomes: (i) verification—an authenticating factor is used as an identity claim, for example, such as a name tag, and the present invention may validate or reject the claimed identity; (ii) identification—when other identifying means are not available, a newly acquired signal may be compared against the pre-recorded database, and the outcome of the present invention may be the provision of the identity information pertaining to the newborn.

In still another example, an embodiment of a small-scale version of the present invention may be implemented for field agent authentication. For example, in welfare monitoring environments, such as for soldiers whose vital signals are being monitored continuously from a central authority, biometrics based on a physiological signal may be used to validate the soldiers' identities continuously in order to avoid agent impersonation. Enrolment may be performed once and then recognition may take the form of either identification or verification. In such an embodiment of the present invention, identification and verification may be as follows: (i) identification—a monitoring authority (for example, such as may be implemented as a computer network implemented system) may receive vital signals from unknown sources, and the incoming physiological signal may be matched against a number of pre-enrolled biometric templates to establish the identity of the transmitting agent; (ii) verification—when extra identifying credentials can be employed, for example, such as a serial number associated with a sensor unit, the associated biometric template may be used for biometric matching at the receiver and a YES/NO answer may be provided (the embodiment of the present invention in this mode may answer the question "Is the monitored agent the person I expect him/her to be?").

In some embodiments of the present invention implemented in remote monitoring environments, and in particular in military field operations, the method and system disclosed herein to biometrically recognize physiological signals may be used to differentiate a friend from a foe. In accordance with the distributed aspect of the present invention, biometric matching may be performed on portable electronic devices, for example, such as devices which may be wearable by soldiers. The devices may be operable to achieve peer-to-peer authentication.

Large-scale Recognition Frameworks

Embodiments of the present invention that incorporate large-scale recognition frameworks may generally used by a large population requiring identification, for example, such as a population utilizing such as credit cards, subway passes, health cards, driver's licenses, etc. The assumption is that in such environments one does not have access to all enrollee individuals' biometric samples upon the first deployment of the biometric security system. Recognition may be performed centrally on a server, or locally on a personal electronic device. The biometric templates may also be stored on the server or personal electronic device.

This framework addresses the problem of large-scale recognition by enabling training of the present invention relative to a generic dataset of physiological biometric signals. The training may utilize a machine learning utility or a machine learning algorithm or calculation. Embodiments of the present invention may utilize a generic dataset of physiological signals for the purposes of biometric recognition, which is a significant benefit over the prior art that does not utilize a generic dataset of physiological signals for the purpose of biometric recognition.

A large-scale recognition system or method of the present invention may be centralized or distributed in nature. A centralized embodiment may be similar to the small-scale recognition framework of the present invention. The enrollee individuals' biometric templates may be stored centrally on a remote server and the electronic devices that capture the physiological signals may be network-connected by a wired or wireless connection. The machine learning method to process biometric signals may be operable to enable the recognizer to learn a generic dataset.

Figure 9:
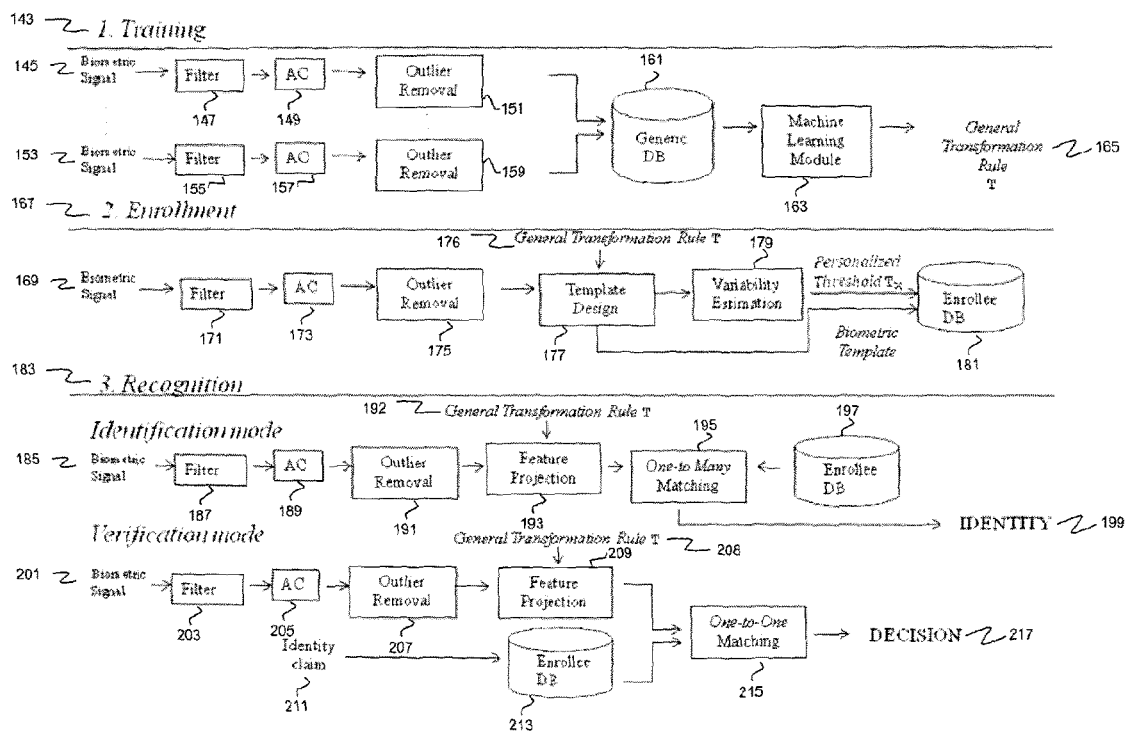
FIG. 9 is a further system diagram illustrating a large scale recognition framework in accordance with the present invention.

An example of a centralized large-scale framework embodiment of the present invention is shown in FIG. 9. In a training mode 143 a training biometric signal 145, such as a physiological signal, is processed in sequential order by a training filter module 147, a training AC module 149 and a training outlier removal module 151. The result of this processing is transferred to a training generic database 161. Embodiments of the present invention may be operable to process multiple biometric signals. As shown in FIG. 9, an additional second training biometric signal 153, such as a physiological signal, may be processed in sequential order by a second training filter module 155, a second training AC module 157 and a second training outlier removal module 159. The result of this processing of a second training biometric signal is transferred to the training generic database. A skilled reader will recognize that additional processing modules may be incorporated in the present invention process multiple biometric signals.

Data pertaining to the training biometric signal and the training second biometric signal is transferred from the training generic database to a training machine learning module 163 that processes the data to produce a general transformation rule 165, such as may be represented as T.

In a centralized large-scale framework embodiment of the present invention, as shown in FIG. 9, a centralized enrollment mode 167 may involve an enrollment biometric signal 169, such as a physiological signal, being processed in sequential order by an enrollment filter module 171, an enrollment AC module 173, an enrollment outlier removal module 175, and an enrollment template design module 177. The enrollment template design module may further receive an enrollment general transformation rule 176, such as may be represented as T, as input for use in the processing and operation of the enrollment template design module. The result from the enrollment template design module may be transferred to an enrollment variability estimation 179 that transfer output, for example, such as an enrollment personalized threshold that may be represented as Tx, to be stored in a enrollment enrollee database 181. It is also possible for the enrollment template design module 177 to transfer output, for example, such as a biometric template, directly to the enrollment enrollee database 181.

In a centralized recognition mode 183 of a centralized large-scale framework embodiment of the present invention, as shown in FIG. 9, a centralized identification mode may involve a centralized identification biometric signal 185, such as a physiological signal, being processed in sequential order by a centralized identification filter module 187, a centralized identification AC module 189, a centralized identification outlier removal module 191, and a centralized identification feature projection module 193. The centralized identification feature projection module may further receive an identification generic transformation rule 192, such as may be represented as T, as input for use in the processing and operation of the centralized identification feature projection module. The result from the centralized identification feature projection module may be transferred to a centralized identification one-to-many matching module 195 that may receive input from a centralized identification enrollee database 197. The centralized identification one-to-many matching module may output the identity 199 of a user related to the centralized identification biometric signal 185.

The centralized recognition mode 183 may incorporate a centralized verification mode that may involve a centralized verification biometric signal 201, such as a physiological signal, being processed in sequential order by a centralized verification filter module 203, a centralized verification AC module 205, a centralized verification outlier removal module 207, and a centralized verification feature projection module 209. The centralized verification feature projection module may further receive a centralized verification general transformation rule 208, such as may be represented as T, as input for use in the processing and operation of the centralized verification feature projection module. The result from the centralized verification feature projection module may be transferred to a centralized verification one-to-one matching module 215. A verification identity claim 211, for example, such as a password or other identity representation, may be transferred to a centralized verification enrollee database 213. Data from the centralized verification enrollee database pertaining to the verification identity claim may be transferred to the centralized verification one-to-one matching module 215. The centralized verification one-to-one matching module may output a verification decision 217 as to whether the identity claim matches the verification biometric signal.

In such an embodiment of the present invention, during an enrolment or training phase, a large and anonymous pool of biometric samples of physiological signals is collected. The pool of biometric samples of the physiological signals may be used for training the machine learning utility or generating learning algorithms or calculations. The pool of biometric samples of physiological signals and the training step assists with ensuring that sufficient variability of a physiological signal is captured by the recognizer component of the present invention, without being subject or individual specific. The machine learning utility is operable to generate or access one or more transformation rules that can project an arbitrary biometric input.

During enrollment, the transformation rule is used for projection or identification of the input biometric features. This use of the transformation results in the generation of a biometric template. Based on the prior training utilizing an anonymous pool of biometric samples of physiological signals, the enrolled biometric template may be statistically protected against a variety of other morphologies of physiological signals. Similar to the physiological signal processing method of the small-scale embodiment of the present invention (as shown in FIG. 1), recognition in the centralized large-scale framework embodiment of the present invention may be either in an identification or verification stage, depending on the implementation environment. A skilled reader will recognize that the present invention may perform recognition in either a CIR or IIR mode.

As an example of a possible implementation of a centralized large-scale framework implementation of the present invention, a large-scale identification system or method may be operable to control access to the subway. For example, a generic dataset may be created offline, and the system or method of the present invention may be trained. A transformation rule may be generated by operation of the present invention. The transformation rule may be used by the subway authority to design biometric templates. When a user pays a fare a sample of the biometric signal of the individual user is collected. A template is then designed for that individual through use of the transformation rule. The template is stored centrally on a server and recognition is then performed with the following possibilities: (i) identification—a watch-list based operation where a new sample of the physiological signal is collected, it is compared against the pre-enrolled ones, and the output is a YES/NO decision based on one-to-many matches (this embodiment answers the question "Has this person paid the fare?"); (ii) verification—during recognition the user presents a subway pass which is linked to a physiological biometric template stored centrally, a new sample of the physiological signal is collected and matched against the template that the card indicates, and the output is YES/NO (this embodiment answers the question "Is this user the legitimate card holder?").

A distributed large-scale framework embodiment of the present invention may be similar to the small-scale recognition framework of the present invention, in that every user individual may hold an electronic device that is operable to perform biometric authentication using physiological signals. The electronic device is personalized by securely storing thereon the biometric template of the respective user individual. In addition, a personal transformation rule is stored on the electronic device. The personal transformation rule is utilized for biometric recognition. The personal transformation rule is estimated using a machine learning method which enables the recognizer to learn the variability of the particular user individual and a generic dataset.

Figure 10:
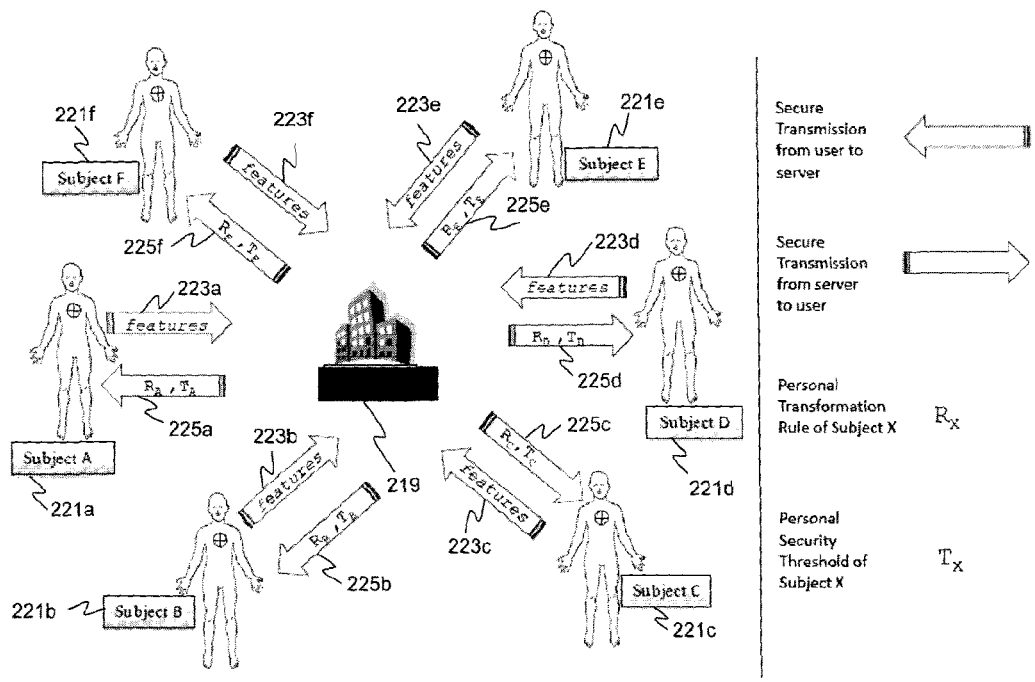
FIG. 10 is a system diagram illustrating multi-user system architecture in accordance with the present invention.

An example of an implementation of a distributed large-scale framework embodiment of the present invention incorporating a personalized recognizer is shown in FIG. 10. Similar to the centralized large-scale framework embodiment of the present invention described herein, the training phase of the distributed large-scale framework includes formation of a generic dataset of physiological signals. Machine learning is initiated by the system after the physiological signal for a particular enrollee individual is acquired, as shown in FIG. 10. One or more biometric signals of one or more subject individuals 221a, 221b, 221c, 221d, 221e, 221f, may be processed to identify one or more features comprising feature data 223a, 223b, 223c, 223d, 223e, 223f, that may be transferred to a server 219. Transfer of information to and from between the server and the subject individual may be by way of secure transmission. Data sent from the server to each subject individual 225a, 225b, 225c, 225d, 225e, 225f, may include, for example, personal transformation rule data pertaining to the subject individual, personal security threshold data pertaining to the subject individual, and other data pertaining to the subject individual.

The enrollment signal may be utilized collectively with the generic dataset to operate machine learning. The process of machine learning may further be operable to enable the learning of particular signal patterns against various other sets of signal patterns, including the associated morphologies. This allows for protection of the biometric templates against attacks, for example, such attacks using random signal patterns. The machine learning module may be implemented as part of a client computer program loaded on a network-connected device, or alternatively may be implemented as a web enabled service made available using a mobile device, by means of a connection to a server computer. Any connections of elements of the present invention may be wired or wireless connections.

Figure 11:
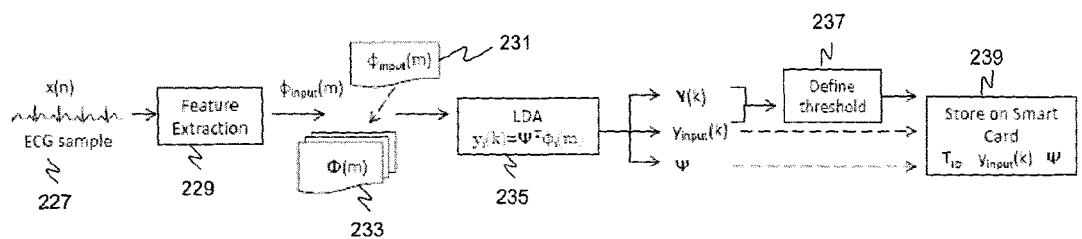
FIG. 11 is a workflow diagram illustrating the enrolment process, in accordance with one aspect of the invention (distributed framework).

An example of an enrollment procedure for biometric signal processing of physiological signals of the present invention is shown in FIG. 11. A physiological signal sample 227 is provided and a feature extraction step 229 is undertaken. Upon the provision of a generic database of physiological signals, the autocorrelation (AC) of every signal is computed using Eq. 1. This results in a number of AC segments ϕ(m) 233 against which an input AC feature vector ϕinput(m) 231 is learned. Let the number of classes in the generic dataset be C. The training set will then involve C+1 classes as follows:

$$\Phi(m) = [\Phi_1(m), \Phi_2(m) \ldots \Phi_C(m), \Phi_{input}(m)] \quad (2)$$

And for every subject i in C+1, a number of Ci AC vectors are available:

$$\Phi_i(m) = \{\phi_v(m)\}_{v=1}^{C_i} \quad (3)$$

Although multiple recordings per subject are optional, the discriminant will perform better when trained on more than two instances of the biometric per subject, since this is only required in the enrollment mode of operation, and does not affect the overall waiting of the recognition system.

Given ϕ(m), LDA will find a set of k feature basis vectors $\{\psi_v\}_{v=1}^{k}$ by maximizing the ratio of between-class and within-class scatter matrix. The maximization is equivalent to solving the following eigenvalue problem:

$$\Psi = \arg\max_{\psi} \frac{|\Psi^T S_b \Psi|}{|\Psi^T S_w \Psi|} \cdot \Psi = \{\psi_1, \ldots, \psi_k\} \quad (4)$$

where Sb and Sw are between-class and within-class scatter matrices. Given the transformation matrix ψ a feature vector 235 is projected using:

$$Y_i(k) = \Psi^T \Phi_i(m)$$

where eventually k<<m and at most C.

An advantage of distributed recognition generally, whether the distributed recognition is incorporated in small-scale or large-scale framework embodiments of the present invention, is that every portable device can be optimized for the intra-class variability of a particular user. On a typical ROC plot of False acceptance rates (FAR) and False Rejection rates (FRR) the FRR depends only on the intra-class variability of the feature vectors. FAR is a measure of inter-class variability of the feature space. Choosing the smallest distance threshold at which an individual is authenticated also guarantees minimum FAR. Essentially, rather than imposing universal distance thresholds for all enrollee individuals, the present invention is operable to "tune" every device with a threshold TID based on the variability of the physiological signals which are to be enrolled, for a particular individual user. The tuning can be achieved by cross fold validation of the distances among the enrolled templates. Finally, in every portable device, the following triplet is stored:

$$\{\Psi, Y_{input}[k], T_{ID}\}$$

A threshold may be defined 237 and data from the processing may be stored on a device or other means 239, such as a smart card.

The enrolment procedure of an embodiment of the present invention incorporating a network-connected device and a remote server may be summarized as including the following steps: (i) the individual initiates the capture of at least one medical biometric signal, or the network-connected device initiates this capture; (2) the biometric signal is stored to a memory associated with the network-connected device; (3) a secure communication session is established between the network-connected device and a remote server linked or linkable, or otherwise connected or connectable, to the network-connected device; (4) the medical biometric signal is communicated to the remote server for enrolment by operation of the remote server; (5) in response to the communication of the medical biometric signal, the remote server is operable to communicate a personal transformation rule to the remote server; and (6) in response, the network-connected device designs a biometric template, which is then stored to the memory of the network-connected device or the server along with the personal transformation rule and the threshold. A skilled reader will recognize that variations on these steps may be possible for other embodiments of the present invention.

In embodiments of the present invention recognition of an individual may occur either by way of an identification or verification stage, and the identification or verification stage may be implemented by a recognizer.

One embodiment of the present invention may be implemented as distributed and be operable to verify one or more individuals in the group using a network-connected device. In such an embodiment of a distributed authentication system the recognition element may be personalized for each individual, based on the personalized threshold.

There are several possible implementations of embodiments of the present invention. For example, embodiments of the present invention may be operable to capture and utilize one or more physiological signals of an individual. As a more specific example, certain physiological signals, such as the PPG and the ECG, can be captured from an individual's fingers. An individual may utilize one of his or her fingers to provide physical or logical access control in an embodiment of the present invention. In such an embodiment of the present invention, being a stand-alone biometric system or method based on physiological signals, individuals are identified using signals that are virtually impossible to mimic and which inherently guarantee the "liveness" of the biometric reading. In this manner the present invention is operable to provide a secure means of human authentication.

Embodiments of the present invention may further capture multiple types of physiological signals. Thus, in an embodiment of the present invention, instead of a stand-alone system or method, a multi modal biometric system or method is provided whereby physiological signal-based biometric recognition operates in conjunction with other biometric modalities. For example, an embodiment or the present invention may include one or more fingerprint scanners and also a means to allow for simultaneous ECG or PPG collection, as shown in FIG. 12.

Figure 12:
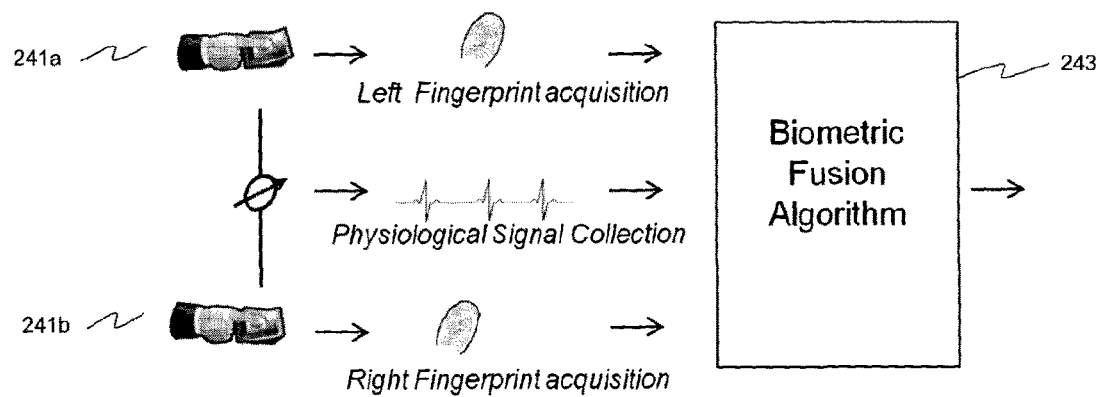
FIG. 12 is a system diagram illustrating a multi-modal biometric recognition framework.

For example, as shown in FIG. 12, one or more fingerprint scanners 241*a*, 241*b* may be utilized to generate data relating to one or more fingerprint scans of a user, for example, such as left fingerprint acquisition, physiological signal collection, and right fingerprint acquisition, or other data relating to one or more fingerprint scans. The data generated from the one or more scans may be transferred to and processed by a biometric fusion algorithm or calculation 243. A skilled reader will recognize that other methods of means of generating physiological signals and related data, and processing such data, are possible in embodiments of the present invention.

The multi-modal system offers the following benefits over the prior art: (i) it is operable to perform identification based on two rather than one modality; (ii) multi-modal biometric systems have been shown to enhance security and accuracy; (iii) bi-modal systems are more effective to deflect replay attacks; (iv) the presence of physiological signals ensures biometric liveness for all modalities and addresses the fingerprints' vulnerability to circumvention; and (v) sensor failure does not necessarily take the system offline, as the other modality can be used for one-factor recognition.

In another embodiment of the present invention, biometric systems based on physiological signals may be deployed on gaming devices, for example, such as portable or non-portable devices. Such an embodiment of the present invention may offer the following advantages over the prior art: (i) physiological signal-based biometric systems can secure gaming devices with a lock/unlock utility that is operable in accordance with user authentication; (ii) for electronic devices that are used by more than one user, physiological signal biometrics allow for profile management such that multiple users are enrolled on an electronic device by providing their physiological signatures, and during verification a newly captured version of one or more physiological signals from a user is compared against the set of known garners authorized to use the electronic device, so that current user is recognized, and at this point the gaming device retrieves information relevant to the gaming preferences of the current user based on his or her profile.

Yet another benefit of capturing physiological signals on gaming devices over the prior art is that the gaming device may provide a source of physiological feedback. Physiological signals are continuous and can be captured throughout a gaming session. The physiological signals, for example, such as ECG, GSR and other signals, can be analyzed in order to provide information on the instantaneous arousal level of the user of the gaming device.

Test Results

A test was performed for an embodiment of the present invention. The test and the results thereof are described herein as an example of an implementation of one embodiment of the present invention. The test was over ECG recordings collected at the BioSec.Lab, at the University of Toronto. Two recording sessions of ECG recordings took place. Each recording session was scheduled a couple of weeks apart. During the first session 52 healthy volunteers were recorded for 3 minutes each. The second session occurred a month later and involved 16 of the original 52 volunteers, each of the 16 volunteers were recorded for 3 minutes each. The ECG recordings were used to investigate the permanence of the signal as this pertains to verification performance of the embodiment of the present invention.

The ECG signals were collected from the volunteer subject's wrists. A Vernier ECG sensor was used to collect the ECG signals. The wrists were selected for this recording because the morphology of the acquired signal may resemble that of a sample collected by a smart card from the subject's fingers. The sampling frequency utilized was 200 Hz.

In order to allow for mental state variability to be captured in the data, during the collection the volunteer subjects were given no special instructions. The ECG recordings of the 36 volunteers who participated in the experiment solely during the initial recording session were used to build the generic dataset. Each ECG signal was partitioned into segments of 5 second lengths. The result was a collection of 1296 ECG samples of 5 seconds each. For the 16 volunteers that participated in the initial and second recording sessions, two ECG recordings were produced and available. The ECG recordings from the initial session for those 16 volunteers were used for enrollment of the volunteer enrollees. A total of 576 samples were enrolled. The ECG recordings from the second session for those 16 volunteers were utilized for testing. A total of 576 samples were utilized for testing.

Preprocessing of the signals is a very important step, because ECG may be affected by both high frequency noise, for example, such as powerline interference and low frequency noise, for example, such as baseline wander frequency noise. To clean up the signals a butterworth bandpass filter of order 4 was utilized. The filter was centered between 0.5 Hz and 40 Hz based on empirical results. After filtering, autocorrelation (AC) was computed according to Equation 1, as is disclosed herein, for the generic dataset, the enrollment records and the testing ones.

Iteratively, each of the volunteer enrollees' ECG recordings were appended to the generic dataset and an LDA was trained. The projected template was then tested for matching against the respective volunteer subject's recordings in the test set. To compute FAR the same template was matched against each of the remaining subjects in the enrollee dataset. This subset of recordings was unseen to the current LDA, and thus constituted the unknown population.

Figure 13:
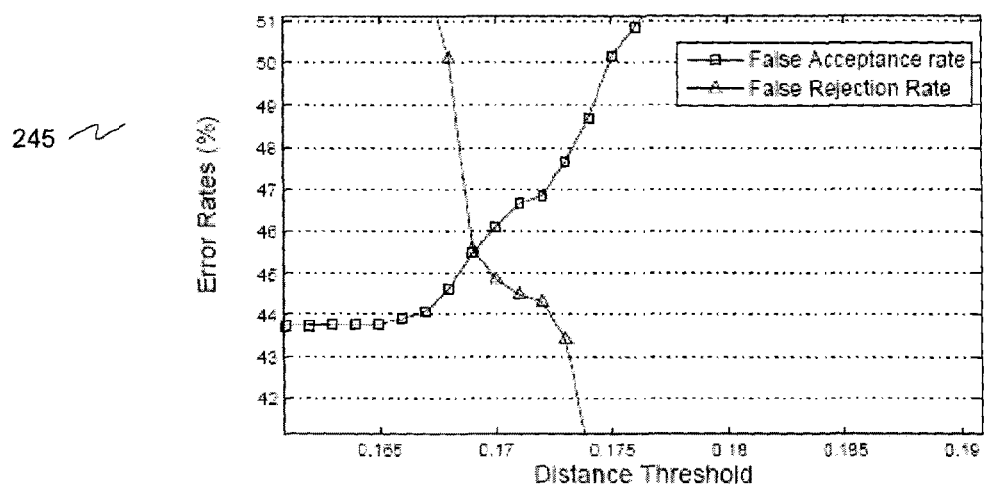
FIG. 13 is a chart illustrating false acceptance and false rejection plots.

As shown in FIG. 13, there may be trade-offs between false acceptance and rejection when the same threshold values are imposed for all card holders in a biometric security system or method. FIG. 13 shows in table 245 plotting of false acceptance rates and false rejection rates. LDA may be trained on the generic dataset only. In some embodiments of the present invention the Equal Error Rate (EER), being the rate at which false acceptance and rejection rates are equal, may be, for example, a rate such as 45.5%. Such performance may not be acceptable for all implementations of embodiments of the present invention if such embodiments are to function as a viable security solution.

In embodiments of the present invention it may be possible to distribute the recognizer in smart cards, if smart cards are utilized in the implementation of the embodiment of the present invention. Such an embodiment of the present invention may take advantage of the fact that every card can be optimized for a particular individual.

Figures 14, 15:
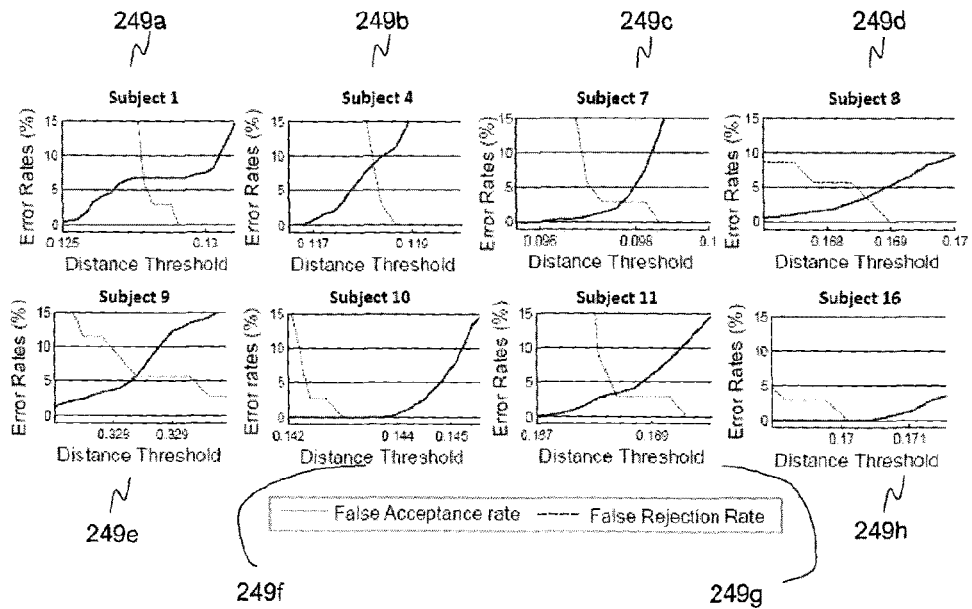
FIG. 14 is a list of the individual EER for all of the 16 testing subjects.
FIG. 15 is a series of tables showing ROC plots for selected individuals in a test set.

A list 247 of the individual EER for all of the 16 testing subjects is shown in FIG. 14. From this list it may be observed that certain individuals may have stronger ECG templates than others. For example, volunteer enrollee subject 10 has a stronger ECG template than volunteer enrollee subject 5. The variations in ECG templates between individuals is a fact that is well known for all biometric modalities. However, by utilizing volunteer enrollee subject specific thresholds, for example, such as thresholds that take into account the particular intra-class variability of every individual, the overall EER may drop dramatically.

Individual ROC plots 249a, 249b, 249c, 249d, 249e, 249f, 249g, 249h, in the testing set are shown in FIG. 15. Given these plots as descriptors, the operator may choose the desired threshold, according to the specifics of every implementation of an embodiment of the present invention. If for example a small number of intruders is expected, FA may be preferred over FR, and in such a situation a smaller threshold selection may be more appropriate. A skilled reader will recognize the choices available to an operator utilizing an embodiment of the present invention in any particular implementation.

It will be appreciated by those skilled in the art that other variations of the embodiments described herein may also be practiced without departing from the scope of the invention. Other modifications are therefore possible. Some examples of possible modifications are provided below:

Fiducial Independent Feature extraction Methods—A skilled reader will recognize that various methods and systems for fiducial independent feature extraction may be used in some embodiments of the present invention instead of autocorrelation (AC), including, as examples, any of the following: Discrete Wavelet Transform (DWT); Fourier Transform; Dynamic Time Warping (DTW); Short time Fourier Transform (STFT); Spectral Density; and Autoregressive Analysis.

Learning Algorithms—A skilled reader will recognize that a variety of possible algorithms may be used in some embodiments of the present invention instead of the Linear Discriminant Analysis, including, as examples, any of the following: Principal Component Analysis (PCA); Kernel Principal Component Analysis (kPCA); Independent Component Analysis (ICA); and Discrete Cosine Transform (DCT).

Classification Algorithms (or Matching Algorithms)—A skilled reader will recognize that various classification or matching algorithms or calculations may be utilized in some embodiments of the present invention instead of the k-Nearest Neighbor classifiers, including, as examples, any of the following: Naïve Bayes Classifier; Support Vector Machines (SVM); Kernel estimation; Decision trees; Artificial Neural Networks (ANN); Perceptrons; and K-means clustering.

We claim:

1. A biometric security system operable to authenticate one or more individuals, said system characterized in that it comprises:
   a) a device operable to obtain one or more physiological signals of each of the one or more individuals, wherein the one or more individuals are initially enrolled in the biometric security system and the one or more individuals are members of a small scale frame work of individuals that were previously identified before the device is employed to currently obtain the one or more physiological signals;
   b) a machine learning utility connected to the device, said machine learning utility being operable to biometrically process the one or more physiological signals to determine a variability of physiological signals for a larger population of the one or more individuals based on the one or more physiological signals obtained from the individual members of the small scale frame work, and to identify or verify the identity of each of the one or more individuals, wherein the machine learning utility is trained with recordings of one or more older physiological signals that were previously obtained from the previously identified individuals that are members of the small scale frame work and the larger population of the one or more individuals; and
   c) one or more databases connected to the machine learning utility operable to store one or more biometrically processed physiological signals.

2. The biometric security system of claim 1, characterized in that the machine learning utility is operable in any of the following modes: continuous identity recognition mode; and instantaneous recognition mode.

3. The biometric security system of claim 2, characterized in that the device is operable to obtain the one or more physiological signals of the one or more individuals on a continuous basis during a period of time when operating in the continuous identity recognition mode.

4. The biometric security system of claim 2, characterized in that the device when operating in the continuous identify recognition mode is operable to estimate cumulative biometric confidence by assessing the progression of one or more biometric decisions in reference to time.

5. The biometric security system of claim 4, characterized in that the cumulative biometric confidence estimate is operable in relation to one or more alarm outputs, whereby when an alarm occurs the cumulative biometric confidence increases, and this initializes a period of suspected intrusion monitoring, during which the cumulative confidence will either increase or remain at a previous level.

6. The biometric security system of claim 1, characterized in that the device incorporates a display means operable to display the authentication results of the system to each of the one or more individuals.

7. The biometric security system of claim 1, characterized in that the device incorporates an input means operable for any of the one or more individuals to input an identity claim to provide identification data that is any of the following: a name; a password; a device ID number; and other non-biometric data identifying the one of the one or more individuals inputting the identity claim.

8. The biometric security system of claim 1, characterized in that the one or more databases include any of the following: a generic database, an enrollee database, or an enrollee and generic database.

9. The biometric security system of claim 8, characterized in that the generic database is operable to store one or more template biometric signals generated by a biometric template design module so that the one or more template biometric signals are accessible by the machine learning utility to determine the variability of each of the one or more physiological signals in a population.

10. The biometric security system of claim 1, characterized in that it is a distributed system or a centralized system.

11. The biometric security system of claim 1, characterized in that a variability estimation means operable to generate a threshold output is connected to the machine learning utility.

12. The biometric security system of claim 1, characterized in that any of the following are connected to the machine learning module and are operable to biometrically process the one or more physiological signals: a filter module; an autocorrelation module; and an outlier removal module.

13. The biometric security system of claim 1, characterized in that a feature projection module is incorporated in an identification or verification mode of the system to apply a transformation rule to biometrically process the one or more physiological signals, said feature projection module being connected to a matching module.

14. The biometric security system of claim 13, characterized in that the feature projection module is connected to any of the following:
  a) a one-to-many matching module operable to determine the identity of the one of the one or more individuals relating to the one or more physiological signals in the identification mode of the system; and
  b) a one-to-one matching module operable to receive an identity claim and to utilize the identity claim to determine whether one of the one or more physiological signals is that of one of the one or more individuals.

15. The biometric security system of claim 1, characterized in that it is operable in a large-scale framework or a small-scale framework.

16. A biometric security method to authenticate one or more individuals, said method characterized in that it comprises the steps of:
  a) employing a device to receive one or more physiological signals from one or more individuals that are initially enrolled in the biometric security system, wherein the one or more individuals are members of a small scale frame work of individuals that were previously identified before the device is employed to currently receive the one or more physiological signals;
  b) employing a machine learning utility to pre-process each of the one or more physiological signals to generate a biometrically processed signal and determine a variability of physiological signals for a larger population of the one or more individuals based on the one or more physiological signals obtained from the individual members of the small scale frame work, wherein the machine learning utility is trained with recordings of older one or more physiological signals that were previously received from the previously identified individuals that are members of the small scale frame work and the larger population of the one or more individuals;
  c) employing the device to extract features from the biometrically processed signal to generate a set of signal features; and
  d) employing the machine learning utility to classify the set of signal features to identify or verify the identity of each of the one or more individuals.

17. The biometric security method of claim 16, characterized in that it comprises one or more of the further steps of:
  a) wherein the pre-processing of each of the one or more physiological signals includes generating the biometrically processed signal by any of the steps of: filtering and windowing;
  b) wherein the extracting of features of the biometrically processed signal includes generating the set of signal features by any of the steps of: autcorrelation estimation; outlier removal; and machine learning incorporating linear discriminant analysis; or
  c) employing the machine learning utility to classify the set of signal features by any of the steps of: matching; individual confidence estimation; and cumulative confidence estimation.

18. The biometric security method of claim 16, characterized in that it comprises the further step of employing the device to continuously receive the one or more physiological signals relating to at least one of the one or more individuals during a time period and employing the machine learning utility for repeating the following steps for each of the one or more physiological signals to perform continuous recognition identification of at least one of the one or more individuals:
  a) pre-processing each of the one or more physiological signals to generate a biometrically processed signal;
  b) extracting features from the biometrically processed signal to generate a set of signal features; and
  c) classifying the set of signal features to identify or verify the identity of each of the one or more individuals.

19. The biometric security method of claim 16, characterized in that it comprises employing the device to perform the further step of receiving an identity claim from at least one of the one or more individuals and utilizing the identity claim in the verification of the identity of the one of the one or more individuals who provided the identity claim.

20. The biometric security method of claim 16, characterized in that it comprises employing the device to perform the further step of generating any of: a transformation rule; and a threshold.

21. The biometric security method of claim 16, characterized in that it comprises employing the device to perform the further step of applying a biometric algorithm or calculation to identify or verify the identity each of the one or more individuals.

22. The biometric security method of claim 16, characterized in that it comprises the further step of employing the device to perform biometric confidence analysis in any of the following manners: continuously; and cumulatively.

* * * * *

UNITED STATES PATENT AND TRADEMARK OFFICE
CERTIFICATE OF CORRECTION

PATENT NO. : 9,646,261 B2
APPLICATION NO. : 14/116058
DATED : May 9, 2017
INVENTOR(S) : Agrafioti et al.

Page 1 of 3

It is certified that error appears in the above-identified patent and that said Letters Patent is hereby corrected as shown below:

On the Title Page

In Item (57), under "ABSTRACT", in Column 2, Line 5, delete "(MR);" and insert -- (IIR); --, therefor.

On Page 2, in Item (56), under "OTHER PUBLICATIONS", in Column 2, Line 1, delete "et al.." and insert -- et al., --, therefor.

On Page 2, in Item (56), under "OTHER PUBLICATIONS", in Column 2, Line 34, delete "Agafioti" and insert -- Agrafioti --, therefor.

On Page 3, in Item (56), under "OTHER PUBLICATIONS", in Column 2, Line 20, insert -- Official Communication for U.S. Patent Application No. 14/670,316 mailed on August 31, 2015 (9 pages). Official Communication for U.S. Patent Application No. 14/675,489 mailed on September 28, 2015 (11 pages). --.

In the Drawings

In Fig. 5, Sheet 5 of 12, delete "100% (" and insert -- 100% --, therefor.

In the Specification

In Column 1, Line 60, delete "phonocardiogram (PPG)," and insert -- phonocardiogram (PCG), --, therefor.

In Column 2, Line 25, delete "2005."," and insert -- 2005, --, therefor.

In Column 2, Line 31, delete "Conf" and insert -- Conf. --, therefor.

In Column 3, Line 9, delete ""F." and insert -- F. --, therefor.

Signed and Sealed this
Twenty-ninth Day of May, 2018

Andrei Iancu
*Director of the United States Patent and Trademark Office*

In Column 3, Line 43, delete "variaility" and insert -- variability --, therefor.

In Column 5, Line 10, delete "autcorrelation" and insert -- autocorrelation --, therefor.

In Column 5, Line 64, delete "biometric processing" and insert -- biometric signal processing --, therefor.

In Column 7, Line 1, delete "phonocardiogram (PPG)," and insert -- phonocardiogram (PCG), --, therefor.

In Column 7, Line 2, delete "phtoplethysmogram (PPG)," and insert -- photoplethysmogram (PPG), --, therefor.

In Column 7, Line 6, delete "enrolees" and insert -- enrollees --, therefor.

In Column 10, Line 29, delete "sever" and insert -- server --, therefor.

In Column 13, Line 66, delete "an result," and insert -- a result, --, therefor.

In Column 14, Line 11, delete "sever" and insert -- server --, therefor.

In Column 15, Lines 5-6, delete "Biometric processing" and insert -- Biometric signal processing --, therefor.

In Column 15, Line 55, delete "Where" and insert -- where --, therefor.

In Column 15, Line 61, delete "FIG. 3.," and insert -- FIG. 3, --, therefor.

In Column 16, Line 21, delete "p.p." and insert -- pp. --, therefor.

In Column 16, Line 28, delete "$Z_{ij}$ a" and insert -- $Z_{ij}$, a --, therefor.

In Column 16, Line 38, delete "Sb" and insert -- $S_b$ --, therefor.

In Columns 17 & 18, in Table, under "Alarm Type I", Line 6, delete "due noisy" and insert -- due to noisy --, therefor.

In Column 18, Line 4, delete "Th2 59" and insert -- Th2 51 --, therefor.

In Column 21, Line 43, delete "employee?");" and insert -- employee?"). --, therefor.

In Column 22, Line 38, delete "generally used" and insert -- generally be used --, therefor.

In Column 26, Line 1, delete "(2)" and insert -- (3) --, therefor.

In Column 26, Line 5, delete "(3)" and insert -- (4) --, therefor.

CERTIFICATE OF CORRECTION (continued)

In Column 26, Line 18, delete "(4)" and insert -- (5) --, therefor.

In Column 26, Line 21, delete "Sb and Sw" and insert -- $S_b$ and $S_w$ --, therefor.

In Column 26, Line 40, delete "TID" and insert -- $T_{ID}$ --, therefor.

In Column 26, Line 54, delete "(i)" and insert -- (1) --, therefor.

In Column 28, Line 11, delete "garners" and insert -- gamers --, therefor.

In Column 29, Line 45, delete "FA" and insert -- FAR --, therefor.

In Column 29, Line 46, delete "FR," and insert -- FRR, --, therefor.

In the Claims

In Column 30, Line 22, in Claim 1, delete "frame work" and insert -- framework --, therefor.

In Column 30, Line 32, in Claim 1, delete "frame work," and insert -- framework, --, therefor In Column 30, Line 38, in Claim 1, delete "frame work" and insert -- framework --, therefor.

In Column 30, Line 53, in Claim 4, delete "continuous identify" and insert -- continuous identity --, therefor.

In Column 31, Line 58, in Claim 16, delete "frame work" and insert -- framework --, therefor.

In Column 32, Line 2, in Claim 16, delete "frame work," and insert -- framework, --, therefor.

In Column 32, Line 6, in Claim 16, delete "frame work" and insert -- framework --, therefor.

In Column 32, Line 24, in Claim 17, delete "autcorrelation" and insert -- autocorrelation --, therefor.